US012558091B2

(12) United States Patent　　　　(10) Patent No.: US 12,558,091 B2
Denzinger et al.　　　　　　　　　　(45) Date of Patent: Feb. 24, 2026

(54) ACCESSORY DEVICE TO SENSE AND COMMUNICATE TISSUE FORCE AND THICKNESS

(71) Applicant: Cilag GmbH International, Zug (CH)

(72) Inventors: Christopher Denzinger, Loveland, OH (US); Mark Overmyer, Cincinnati, OH (US); Heather Dickson, Cincinnati, OH (US); Craig Smith, Cincinnati, OH (US); Jonathan Von Stein, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/627,011

(22) Filed: Apr. 4, 2024

(65) Prior Publication Data

US 2025/0312037 A1　　　Oct. 9, 2025

(51) Int. Cl.
　　*A61B 17/068*　　　(2006.01)
　　*A61B 17/072*　　　(2006.01)
　　*A61B 17/00*　　　(2006.01)
(52) U.S. Cl.
　　CPC .. *A61B 17/068* (2013.01); *A61B 2017/00022* (2013.01)
(58) Field of Classification Search
　　CPC ................ A61B 17/068; A61B 17/072; A61B 2017/07271; A61B 2017/00022; A61B 17/07292
　　See application file for complete search history.

(56) References Cited

U.S. PATENT DOCUMENTS

| | | | |
|---|---|---|---|
| 8,210,411 | B2 | 7/2012 | Yates et al. |
| 9,186,142 | B2 | 11/2015 | Fanelli et al. |
| 9,517,065 | B2 | 12/2016 | Simms et al. |
| 9,622,746 | B2 | 4/2017 | Simms et al. |
| 9,717,497 | B2 | 8/2017 | Zerkle et al. |

(Continued)

OTHER PUBLICATIONS

Dr. Li Su et al., "Self-powered, ultrasensitive, and high-resolution visualized flexible pressure sensor based on color-tunable triboelectrification-induced electroluminescence", Science Direct, https://www.sciencedirect.com/science/article/abs/pii/S2211285520310077, Oct. 8, 2020.

(Continued)

*Primary Examiner* — Gloria R Weeks
(74) *Attorney, Agent, or Firm* — Lempia Summerfield Katz LLC

(57) ABSTRACT

A tissue sensor is used with a surgical stapling instrument to sense tissue characteristics and to provide accurate tissue measurements. The tissue sensor includes a flexible substrate, a sensor array, and a controller. The flexible substrate is disposed between the tissue and the surgical stapler. The sensor array comprises sensors disposed on the flexible substrate, senses a parameter, and generates a signal indicative thereof in response to a clamping force that is applied by the surgical stapler to clamp the tissue and the tissue sensor together. The controller is disposed in or on the flexible substrate and is configured to receive the signal from the sensor array, process the signal to determine a measurement of the parameter based on the processed signal, and provide an indication of the measurement of the parameter to a user of the surgical stapler.

23 Claims, 33 Drawing Sheets

(56) References Cited

U.S. PATENT DOCUMENTS

| | | | | |
|---|---|---|---|---|
| 9,795,379 | B2 | 10/2017 | Leimbach et al. | |
| 9,808,248 | B2 | 11/2017 | Hoffman | |
| 9,839,421 | B2 | 12/2017 | Zerkle et al. | |
| 9,844,374 | B2* | 12/2017 | Lytle, IV | A61B 17/07207 |
| 10,092,292 | B2 | 10/2018 | Boudreaux et al. | |
| 10,182,813 | B2 | 1/2019 | Leimbach et al. | |
| 11,090,047 | B2* | 8/2021 | Shelton, IV | A61B 17/072 |
| 11,248,978 | B2 | 2/2022 | Kim | |
| 11,304,697 | B2 | 4/2022 | Fanelli et al. | |
| 11,317,912 | B2 | 5/2022 | Jenkins et al. | |
| 11,439,391 | B2 | 9/2022 | Bruns et al. | |
| 11,564,756 | B2* | 1/2023 | Shelton, IV | A61B 5/684 |
| 11,653,920 | B2* | 5/2023 | Shelton, IV | A61L 2/186 |
| | | | | 227/175.1 |
| 11,660,089 | B2* | 5/2023 | Shelton, IV | A61B 17/07207 |
| | | | | 227/180.1 |
| 11,751,874 | B2* | 9/2023 | Eschbach | A61B 17/07207 |
| | | | | 227/176.1 |
| 11,751,929 | B2* | 9/2023 | Shelton, IV | A61B 18/1445 |
| | | | | 606/41 |
| 2015/0272575 | A1* | 10/2015 | Leimbach | A61B 90/96 |
| | | | | 227/175.3 |
| 2019/0200977 | A1* | 7/2019 | Shelton, IV | A61B 34/20 |
| 2022/0304680 | A1* | 9/2022 | Shelton, IV | A61B 17/07207 |
| 2022/0313145 | A1* | 10/2022 | Shelton, IV | A61B 17/0644 |
| 2023/0050358 | A1* | 2/2023 | Shelton, IV | A61B 17/0686 |
| 2023/0414294 | A1* | 12/2023 | Shelton, IV | A61B 34/76 |

OTHER PUBLICATIONS

Fujifilm, "Prescale", Pressure measurement film, https://www.fujifilm. com/us/en/business/industrial-materials/measurement-film/prescale/ feature.

Tactile Pressure Experts, "Fujifilm Prescale Tactile Pressure Indicating Sensor Film", Sensor Products Inc., https://www.sensorprod. com/fuji-prescale.php, 2024.

* cited by examiner

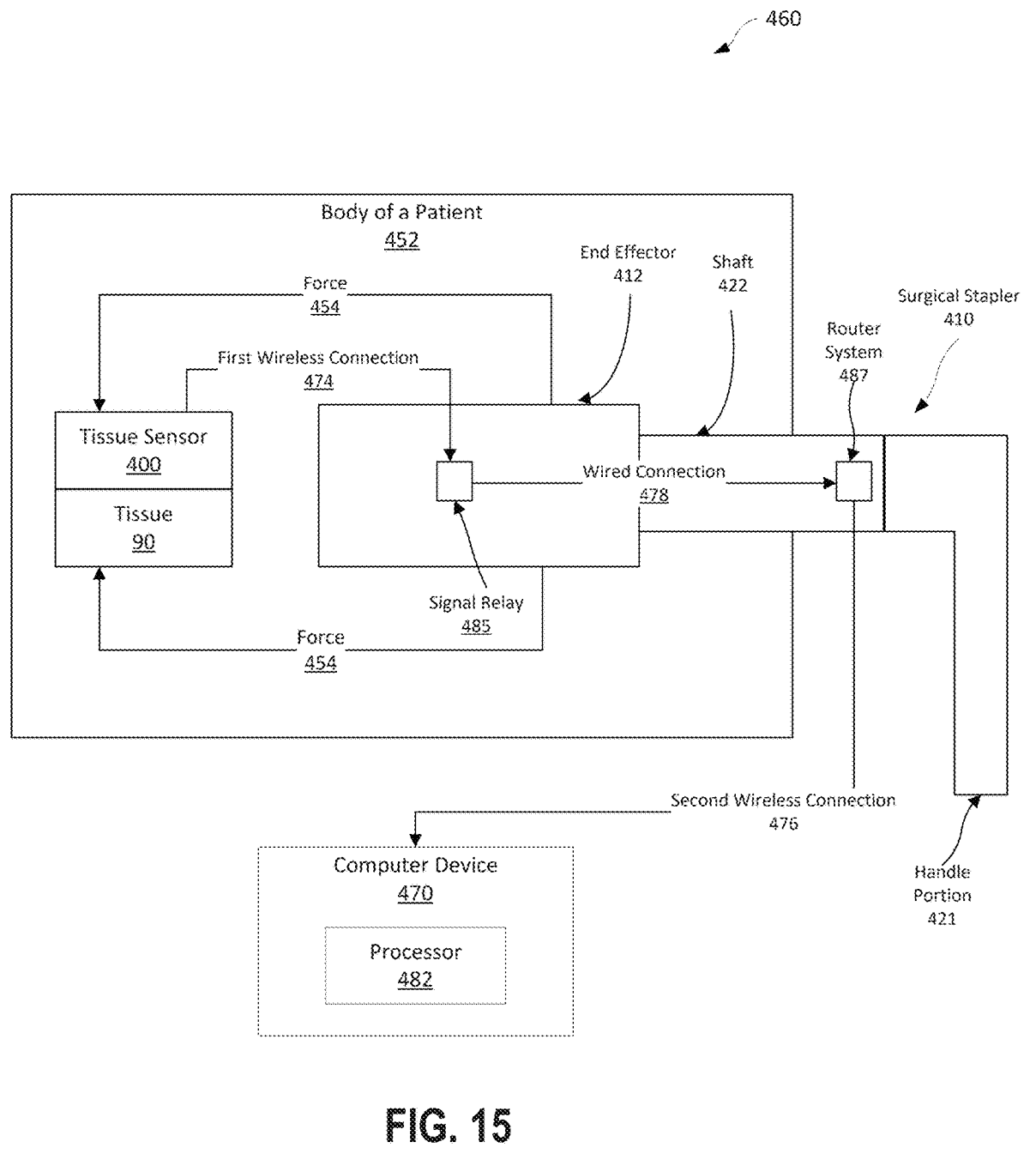

460

Body of a Patient
452

End Effector
412

Shaft
422

Surgical Stapler
410

Router
System
487

Force
454

First Wireless Connection
474

Tissue Sensor
400

Tissue
90

Wired Connection
478

Signal Relay
485

Force
454

Second Wireless Connection
476

Handle
Portion
421

Computer Device
470

Processor
482

FIG. 15

700

Targeting a tissue
702

Disposing a tissue sensor between a surgical stapler and a tissue
704

Clamping the tissue and the tissue sensor
706

Sensing a force applied by the surgical stapler
708

Converting the input mechanical force into an electrical output signal
710

Transmitting a plurality of electrical output signals
712

Controlling the surgical stapler based on the electrical output signal
714

Unclamping the tissue
716

Removing the tissue
718

Re-Clamping the tissue for transection
720

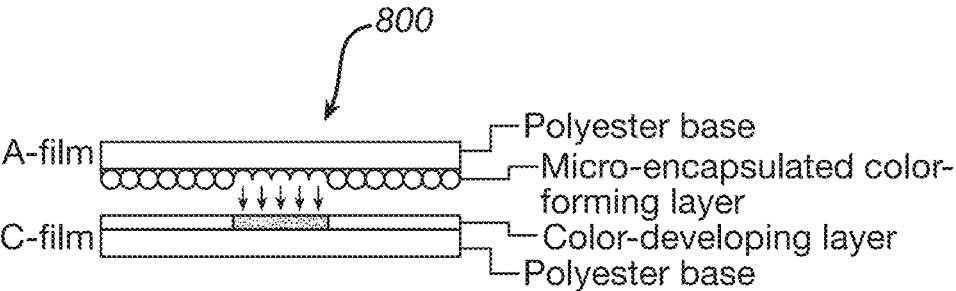
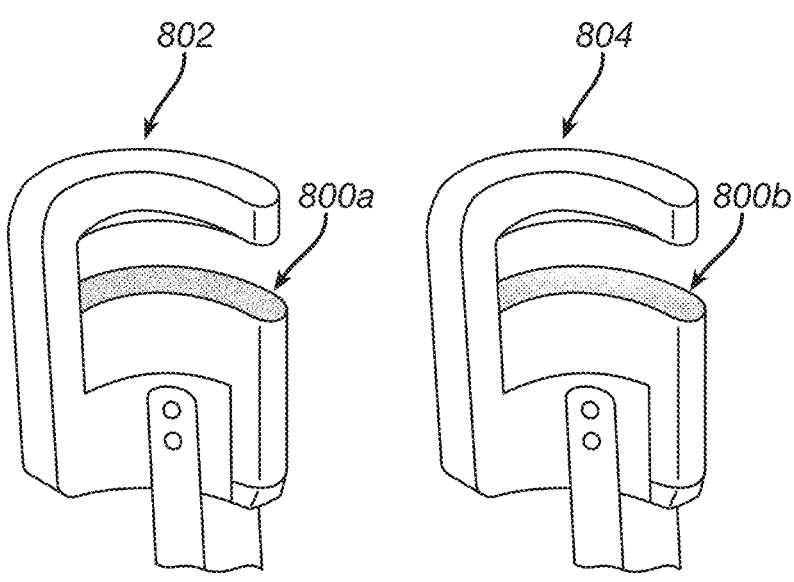
FIG. 22

FIG. 23A          FIG. 23B

ACCESSORY DEVICE TO SENSE AND COMMUNICATE TISSUE FORCE AND THICKNESS

BACKGROUND

Open surgery (e.g., traditional surgery, conventional surgery, open or non-endoscopic procedures, and the like) involves creating a single large incision in the body to access the affected area. During open surgery, a surgeon may work directly with their hands and may have a broader view of the surgical site. In some instances, such as in the case of transplants, large incisions are necessary to remove the damaged organ and replace it with a healthy one. This type of surgery is also used in a variety of treatments, such as the removal of kidney stones.

Surgical staplers are frequently used in surgical procedures for suturing body tissues such as, for example, intestinal and gastric walls. Such devices typically include a staple holder, or cartridge, which is disposed on one side of the tissue to be fastened and an anvil assembly on the other side of the tissue. During the surgical procedure, the staples are driven from the cartridge by some type of actuator so that the ends of the staples pass through the tissue and then are bent inwardly by the anvil so as to produce an array of finished fasteners in the tissue. During the typical suturing process, pusher members associated with the cartridge are controllably advanced by the operating mechanism of the instrument in a manner to urge the staples out of the cartridge, through the tissue and forcibly against the anvil.

One such frequently used type of surgical stapler is the open linear stapler, which is a device that enables the surgeon to simultaneously place one or more rows of surgical staples in body tissue or organs. By way of example, a typical procedure is a pneumectomy, which is a removal of a portion of the patient's lungs. The linear stapler can be used several times during this procedure, including for the occlusion of the pulmonary artery prior to its resection.

In contrast, laparoscopic surgery is a minimally invasive surgery that uses several small incisions. In this case, the surgeon uses laparoscopic or endoscopic surgical instruments to minimize the size of a surgical incision as well as post-operative recovery time and complications. Consequently, some endoscopic surgical instruments may be suitable for placement of a distal end effector at a desired surgical site, e.g., a tissue, through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft that extends proximally from the end effector to a handle portion, which is manipulated by the clinician, or alternatively to a robot. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include endoscopic surgical staplers. Some such staplers are operable to clamp down on layers of tissue, cut through the clamped layers of tissue, and drive staples through the layers of tissue to substantially seal the severed layers of tissue together near the severed ends of the tissue layers. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

In some procedures, it may be necessary to fire (i.e., cut and/or staple) along tissue where more than one firing is necessary to complete the procedure. In other words, it may be necessary to perform multiple sequential firings along a continuous path, known as "marching." With procedures that involve marching, a surgical stapler end effector may be placed at the surgical site, actuated to cut and staple, removed from the surgical site for installation of a new staple cartridge, and then placed back at the surgical site again for the next firing along the same path. In marching and single transection procedures, the clinician may have a need to measure the tissue before cutting, e.g., to make a proper staple cartridge selection to enhance surgical performance. However, known surgical staplers (both endoscopic and open surgical staplers) have limited capabilities for providing information to enable such selections.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 15 depicts a diagram of a tissue sensor detector system according to one embodiment;

FIGS. 20 and 21 depict flow charts depicting operation of a process for the operation of a tissue sensor and a surgical stapler according to one embodiment;

FIG. 22 depicts an example of a pressure sensitive film disposed in open surgical staplers according to one embodiment;

Figure 1:
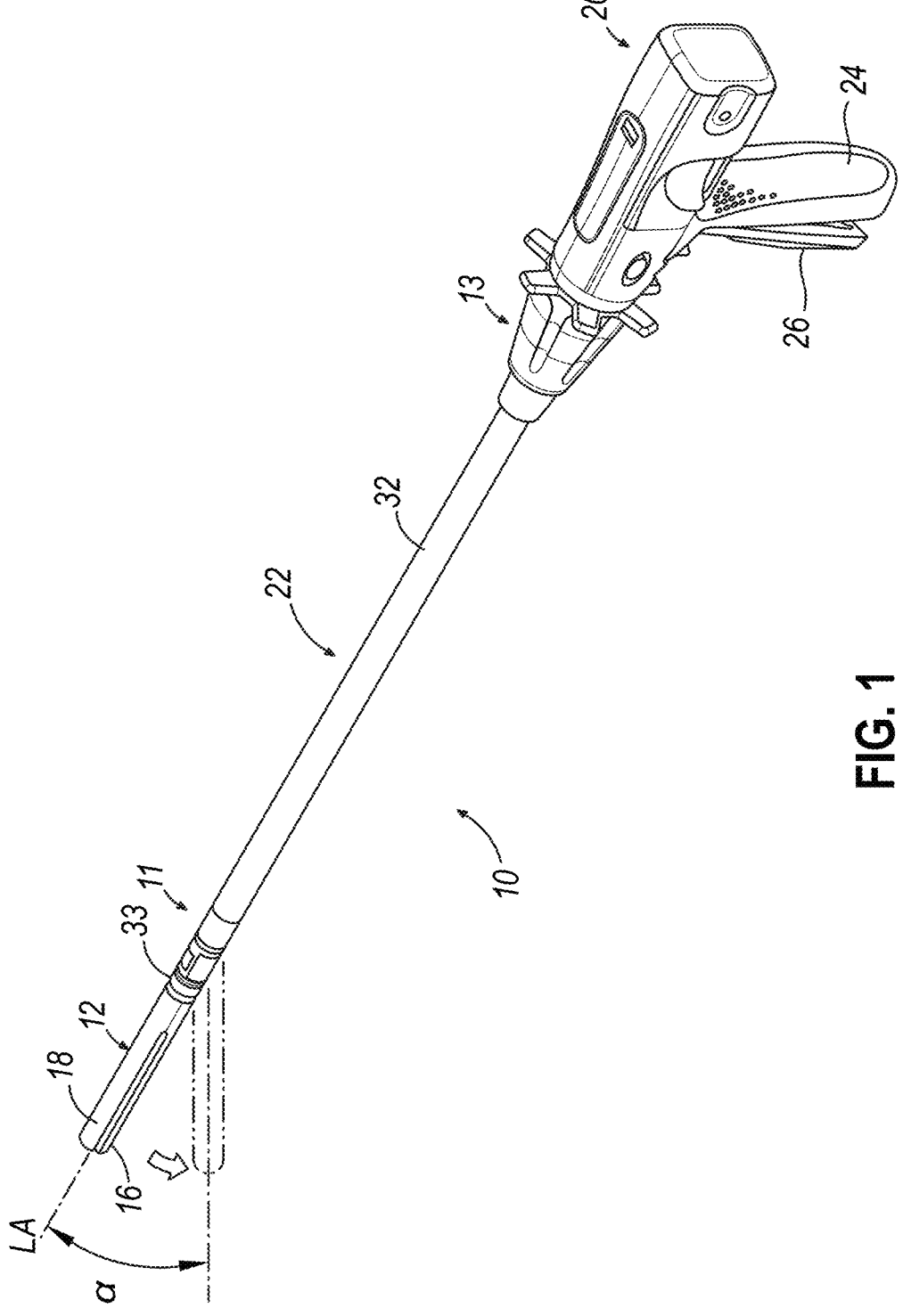
FIG. 1 depicts a perspective view of an example of an articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those having ordinary skill in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers to the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

Furthermore, the terms "about," "approximately," "substantially," and the like as used herein in connection with any numerical values, ranges of values, and/or geometric/positional quantifications are intended to encompass the exact value(s) or quantification(s) referenced as well as a suitable tolerance that enables the referenced feature or combination of features to function for the intended purpose described herein. For example, "substantially parallel" encompasses nominally parallel structures.

As used herein in connection with various examples of end effector jaw tips, a tip described as "angled," "bent," or "curved" encompasses tip configurations in which a longitudinal path (e.g., linear, or arcuate) along which the tip extends is non-coaxial and non-parallel with a longitudinal axis of the jaw body; particularly, configurations in which the longitudinal tip path extends distally toward the opposing jaw. Conversely, a tip described as "straight" encompasses tip configurations in which a longitudinal axis of the tip is substantially parallel or coaxial with the longitudinal axis of the jaw body.

I. Illustrative Surgical Stapler

FIGS. 1-7 depict an example of a surgical stapling and severing instrument 10 that is sized for insertion through a trocar cannula or an incision (e.g., thoracotomy, etc.) to a surgical site in a patient for performing a surgical procedure. Instrument 10 of the present example includes a handle portion 20 connected to a shaft 22, which distally terminates in an articulation joint 11, which is further coupled with an end effector 12. Once articulation joint 11 and end effector 12 are inserted through the cannula passageway of a trocar, articulation joint 11 may be remotely articulated, as depicted in phantom in FIG. 1, by an articulation control 13, such that end effector 12 may be deflected from the longitudinal axis (LA) of shaft 22 at a desired angle (α). End effector 12 of the present example includes a lower jaw 16 (also referred to herein as a cartridge jaw or a second jaw) that includes a staple cartridge 37 (shown in FIG. 3), and an upper jaw 18 in the form of a pivotable anvil jaw 18.

Unless otherwise described, the term "pivot" (and variations thereof) as used herein encompasses but is not necessarily limited to pivotal movement about a fixed axis. For instance, in some versions, anvil jaw 18 may pivot about an axis that is defined by a pin (or similar feature) that slidably translates along an elongate slot or channel as anvil jaw 18 moves toward lower jaw 16. Such translation may occur before, during, or after the pivotal motion. It should therefore be understood that such combinations of pivotal and translational movement are encompassed by the term "pivot" and variations thereof as used herein.

Handle portion 20 includes a pistol grip 24 and a closure trigger 26. Closure trigger 26 is pivotable toward pistol grip 24 to cause clamping, or closing, of anvil jaw 18 toward lower jaw 16 of end effector 12. Such closing of anvil jaw 18 is provided through a closure tube 32 and a closure ring 33, which both longitudinally translate relative to handle portion 20 in response to pivoting of closure trigger 26 relative to pistol grip 24. Closure tube 32 extends along the length of shaft 22; and closure ring 33 is positioned distal to articulation joint 11. Articulation joint 11 is operable to communicate/transmit longitudinal movement from closure tube 32 to closure ring 33.

Figure 2:
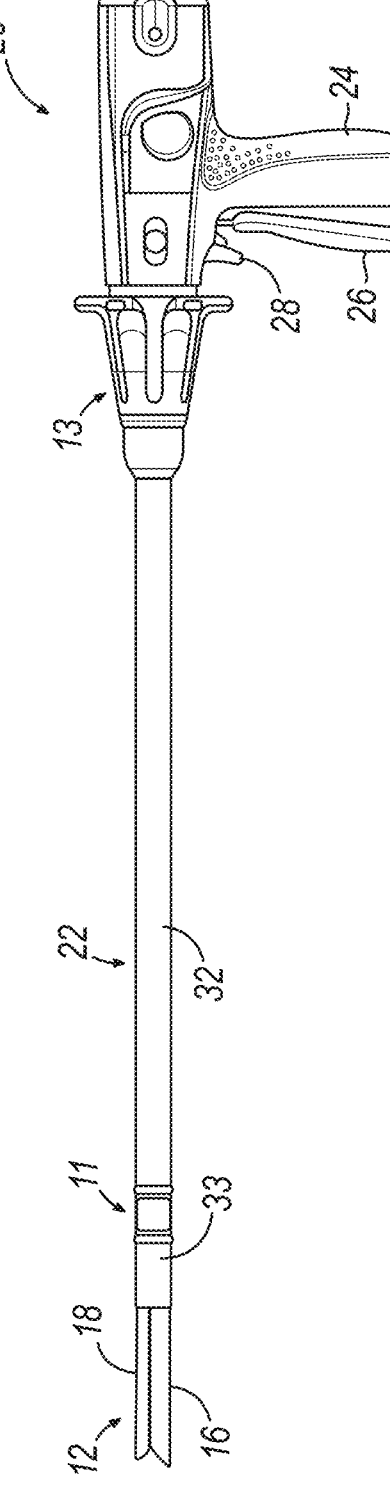
FIG. 2 depicts a side view of the instrument of FIG. 1.

As shown in FIG. 2, the handle portion 20 also includes a firing trigger 28. An elongate member (not shown) longitudinally extends through shaft 22 and communicates a longitudinal firing motion from handle portion 20 to a firing beam 14 in response to actuation of firing trigger 28. This distal translation of firing beam 14 causes the stapling and severing of clamped tissue in end effector 12, as will be described in greater detail below.

As shown in FIGS. 3-6, end effector 12 employs a firing beam 14 that includes a transversely oriented upper pin 38, a firing beam cap 44, a transversely oriented middle pin 46, and a distally presented cutting edge 48. Upper pin 38 is positioned and translatable within a longitudinal anvil slot 42 of anvil jaw 18. Firing beam cap 44 slidably engages a lower surface of lower jaw 16 by having firing beam 14 extend through lower jaw slot 45 (shown in FIG. 4B) that is formed through lower jaw 16. Middle pin 46 slidingly engages a top surface of lower jaw 16, cooperating with firing beam cap 44.

Figure 3:
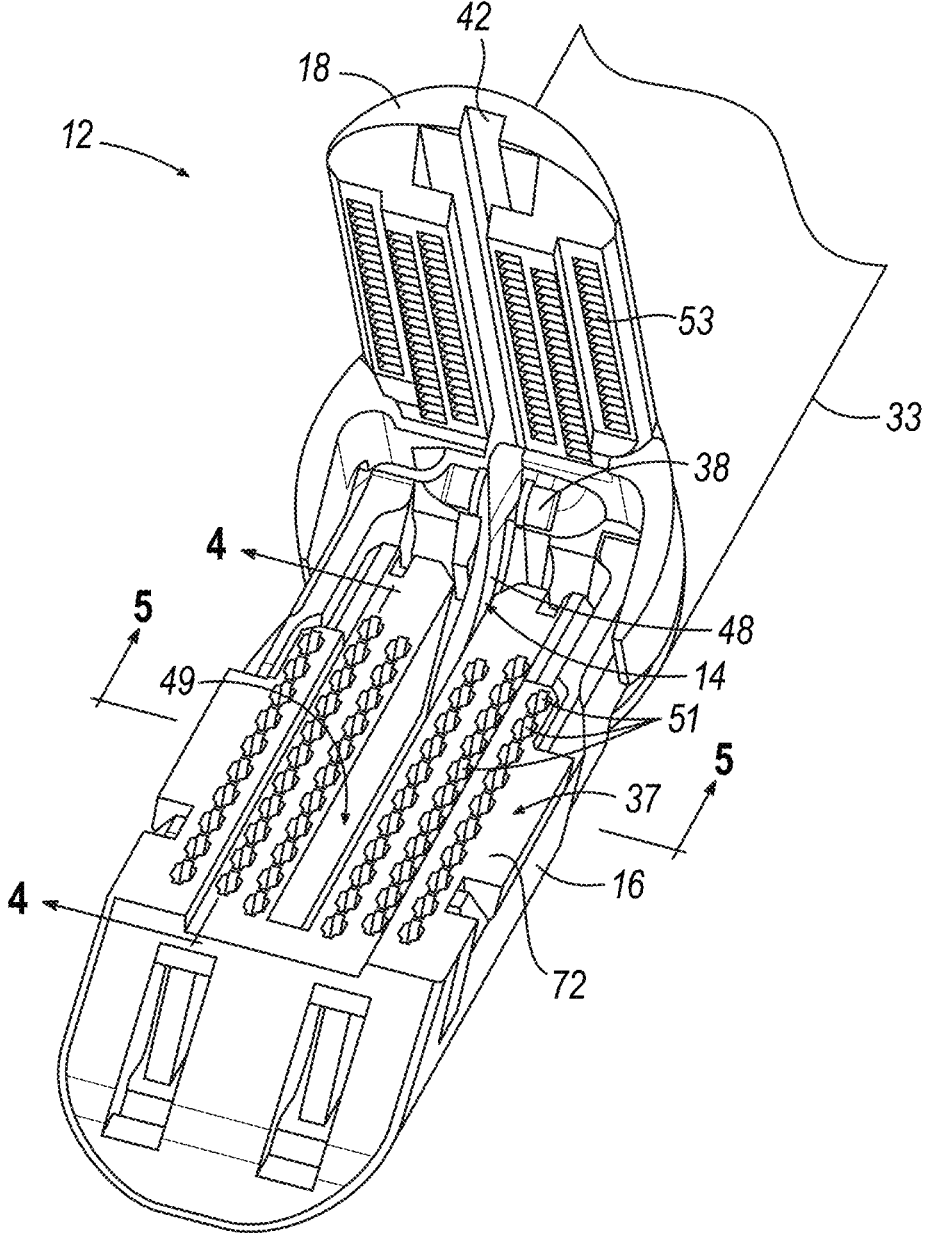
FIG. 3 depicts a perspective view of an opened end effector of the instrument of FIG. 1.
Figure 4A:
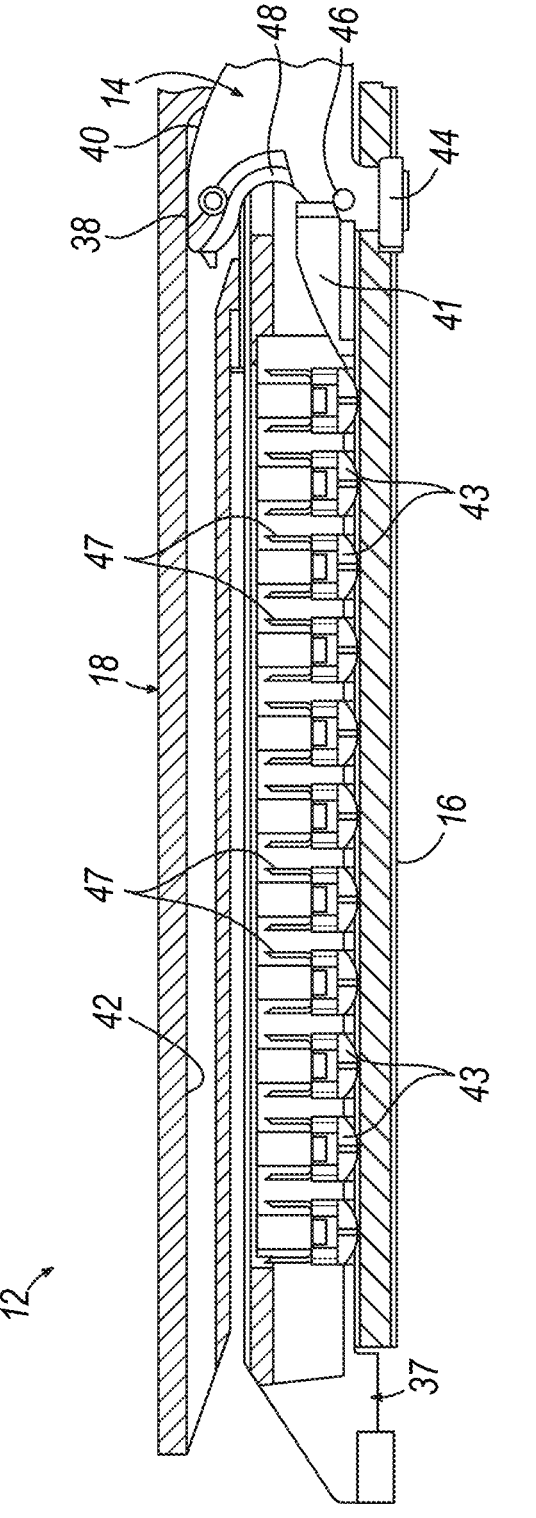
FIG. 4A depicts a side cross-sectional view of the end effector of FIG. 3, taken along line 4-4 of FIG. 3, with the firing beam in a proximal position.
Figure 4B:
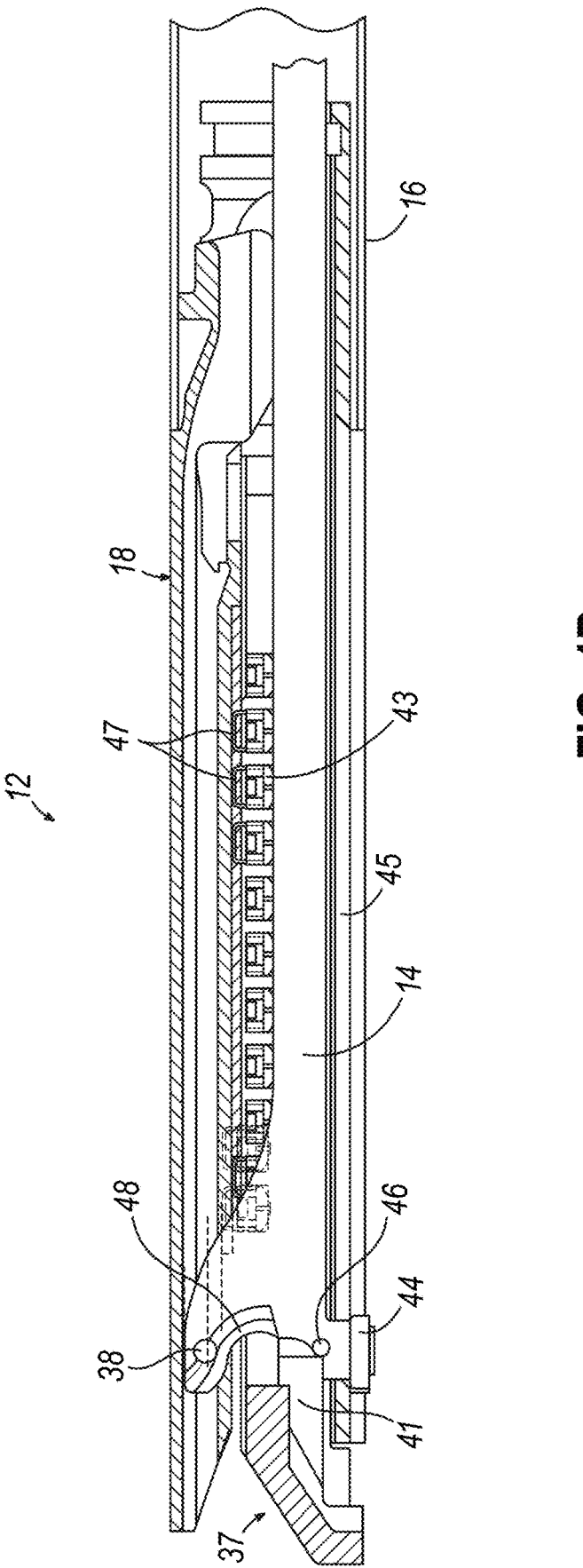
FIG. 4B depicts a side cross-sectional view of the end effector of FIG. 3, taken along line 4-4 of FIG. 3, with the firing beam in a distal position.
Figure 5:
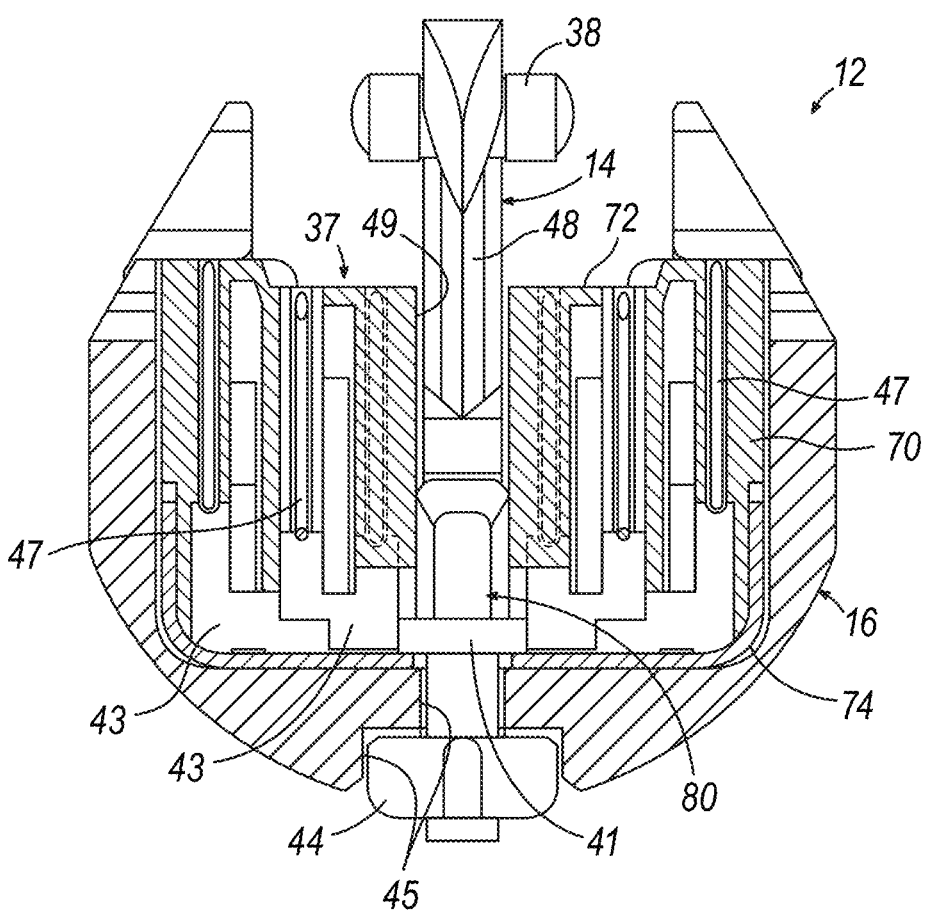
FIG. 5 depicts an end cross-sectional view of the end effector of FIG. 3, taken along line 5-5 of FIG. 3.
Figure 6:
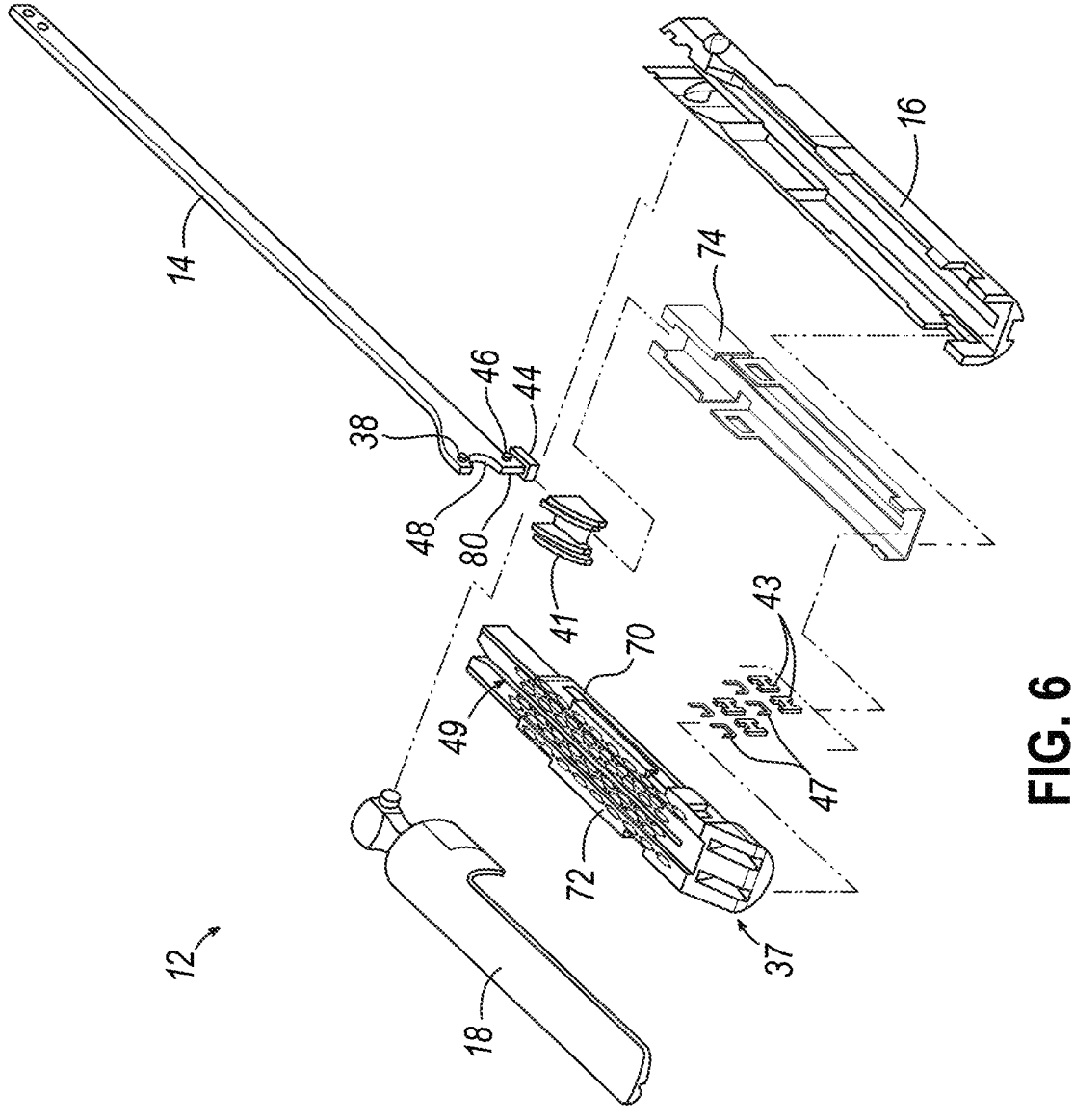
FIG. 6 depicts an exploded perspective view of the end effector of FIG. 3.

FIG. 3 shows firing beam 14 of the present example proximally positioned and anvil jaw 18 pivoted to an open configuration, allowing an unspent staple cartridge 37 to be removably installed into a channel of lower jaw 16. As best seen in FIGS. 5-6, staple cartridge 37 of the present example includes a cartridge body 70, which presents an upper deck 72 and is coupled with a lower cartridge tray 74. As best seen in FIG. 3, a vertical slot 49 extends longitudinally through a portion of staple cartridge body 70. As also best seen in FIG. 3, three rows of staple apertures 51 are formed through upper deck 72 on each lateral side of vertical slot 49. As shown in FIGS. 4A-6, a wedge sled 41 and a plurality of staple drivers 43 are captured between cartridge body 70 and tray 74, with wedge sled 41 being located proximal to staple drivers 43. Wedge sled 41 is movable longitudinally within staple cartridge 37; while staple drivers 43 are movable vertically within staple cartridge 37. Staples 47 are also positioned within cartridge body 70, above corresponding staple drivers 43. Each staple 47 is driven vertically within cartridge body 70 by a staple driver 43 to drive staple 47 out through an associated staple aperture 51. As best seen in FIGS. 4A-4B and 6, wedge sled 41 presents inclined cam surfaces that urge staple drivers 43 upwardly as wedge sled 41 is driven distally through staple cartridge 37.

With end effector 12 closed, as depicted in FIGS. 4A-4B by distally advancing closure tube 32 and closure ring 33, a firing member in the form of firing beam 14 is then advanced distally into engagement with anvil jaw 18 by having upper pin 38 enter longitudinal anvil slot 42. A pusher block 80 (shown in FIG. 5) located at distal end of firing beam 14 pushes wedge sled 41 distally as firing beam 14 is advanced distally through staple cartridge 37 when firing trigger 28 is actuated. During such firing, cutting edge 48 of firing beam 14 enters vertical slot 49 of staple cartridge 37, severing tissue clamped between staple cartridge 37 and anvil jaw 18. As shown in FIGS. 4A-4B, middle pin 46 and pusher block 80 together actuate staple cartridge 37 by entering into vertical slot 49 within staple cartridge 37, driving wedge sled 41 into upward camming contact with staple drivers 43, which in turn drives staples 47 out through staple apertures 51 and into forming contact with staple forming pockets 53 (shown in FIG. 3) on inner surface of anvil jaw 18. FIG. 4B depicts firing beam 14 fully distally translated after completing severing and stapling of tissue. Staple forming pockets 53 are intentionally omitted from the view in FIGS.

4A-4B but are shown in FIG. 3. Anvil jaw 18 is intentionally omitted from the view in FIG. 5.

Figure 7:
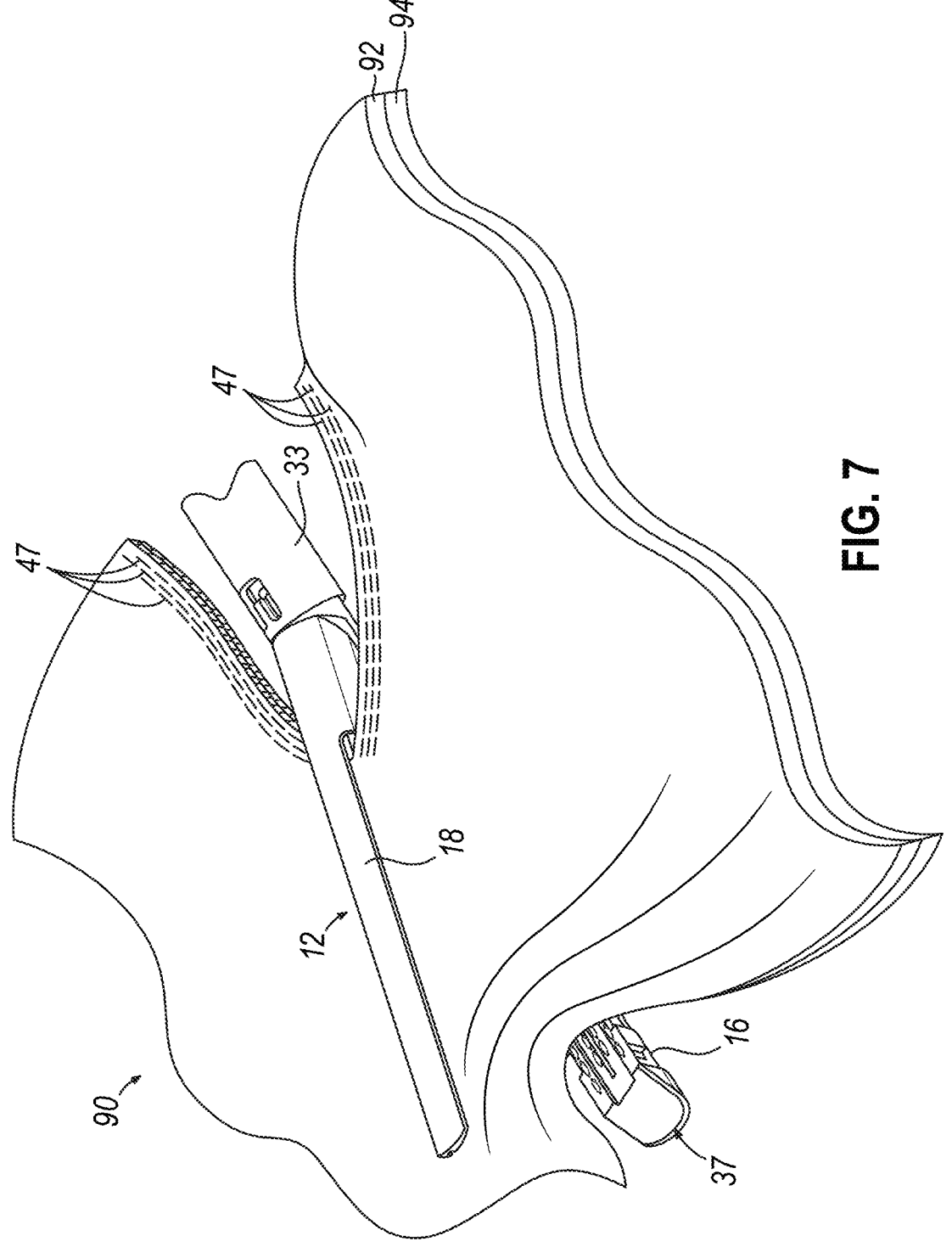
FIG. 7 depicts a perspective view of the end effector of FIG. 3, positioned at tissue and having been actuated once in the tissue.

FIG. 7 shows end effector 12 having been actuated through a single firing stroke through tissue 90. Cutting edge 48 (obscured in FIG. 7) has cut through tissue 90, while staple drivers 43 have driven three alternating rows of staples 47 through tissue 90 on each side of the cut line produced by cutting edge 48. After the first firing stroke is complete, end effector 12 is withdrawn from the patient, spent staple cartridge 37 is replaced with a new staple cartridge 37, and end effector 12 is then again inserted into the patient to reach the stapling site for further cutting and stapling. This process may be repeated until the desired quantity and pattern of firing strokes across the tissue 90 has been completed.

Instrument 10 may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. End Effector with Visualization, Lead-In, and Gathering Feature

In some instances, it may be desirable to provide the user with better visualization of end effector 12. In particular, as end effector 12 is inserted into a surgical site, the user may rotate shaft 22 of instrument 10 during the procedure. As a result, end effector 12 also rotates. As end effector 12 rotates, it may be desirable for the user to have visual access to the surgical site. For instance, the user may wish to see the interface or contact between tissue 90 and end effector 12. Since end effector 12 may be rotated about the longitudinal axis (LA) relative to handle portion 20, the user may view the surgical site such that lower jaw 16 of end effector is visible rather than anvil jaw 18. Alternatively, end effector 12 could be rotated such that when the user views end effector 12, anvil jaw 18 is visible by the user. It may be desirable to provide visibility of the surgical site for the user beyond what is possible in instrument 10 of FIG. 1.

For instance, in the case of some surgical procedures where fluid carrying vessels are transected and stapled, it may be desirable to have visual confirmation that anvil jaw 18 and lower jaw 16 completely cover the vessel to be cut, such that the vessel may be fully cut and stapled in one single actuation. In other words, the user may wish to avoid cutting and stapling only a portion of a vessel. Thus, some means of visual monitoring and/or feedback may be desirable so that the user will know that end effector 12 has been positioned properly within the surgical site for anvil jaw 18 and lower jaw 16 to fully clamp the vessel. One potential way of monitoring the surgical site may include improving visualization of the area adjacent to the distal tip of lower jaw 16 and anvil jaw 18. Furthermore, not only visualization of the distal end of end effector 12 may be desirable, but also it may be desirable to construct end effector 12 such that the distal end of anvil jaw 18 is configured to urge tissue (e.g., a large vessel) proximally into the space between anvil jaw 18 and lower jaw 16 as anvil jaw 18 closes toward lower jaw 16.

Figure 8:
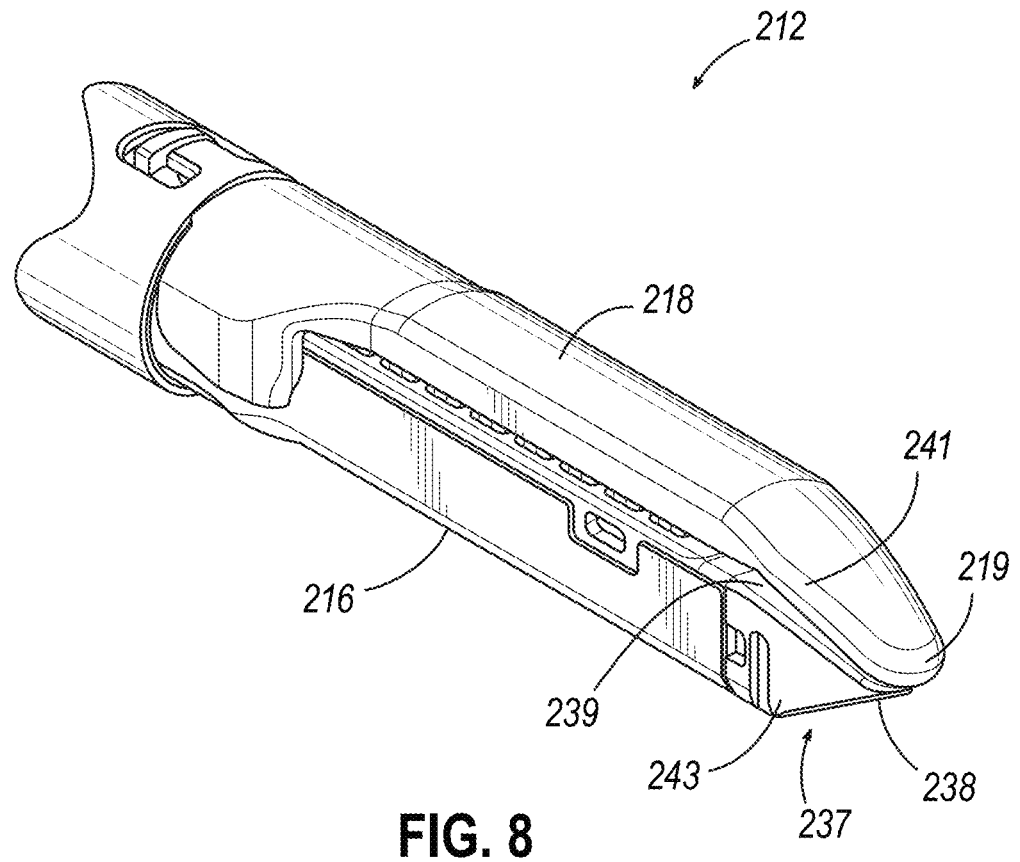
FIG. 8 depicts a perspective view of an alternative version of an end effector with an angled anvil jaw and an angled cartridge.

FIG. 8 depicts an example of an end effector 212 comprising an anvil jaw 218 and a lower jaw 216. It will be appreciated that end effector 212 may be used in place of end effector 12 of instrument 10. End effector 212 may be integrally formed with instrument 10 or in the alternative may be interchangeable with end effector 12 of instrument 10.

Anvil jaw 218 is operable to pivot relative to lower jaw 216. Anvil jaw 218 and lower jaw 216 may clamp tissue 90 similarly to clamping performed by anvil jaw 18 and lower jaw 16 shown in FIG. 1. End effector 212 further includes a cartridge 237 operable to be placed in lower jaw 216 similarly to cartridge 37 shown in FIG. 3.

Figure 9:
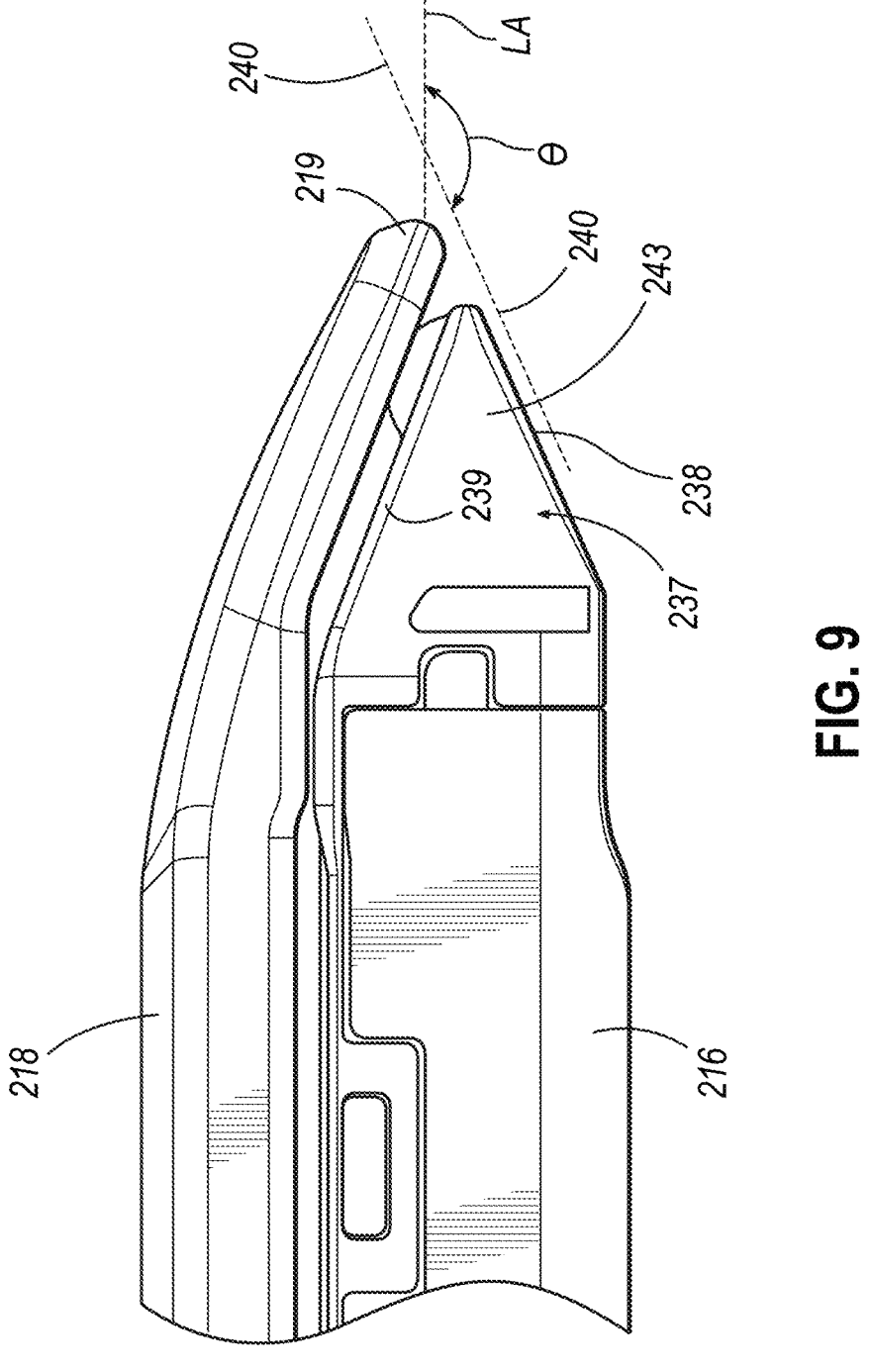
FIG. 9 depicts an enlarged, side view of the end effector of FIG. 8.
Figure 10:
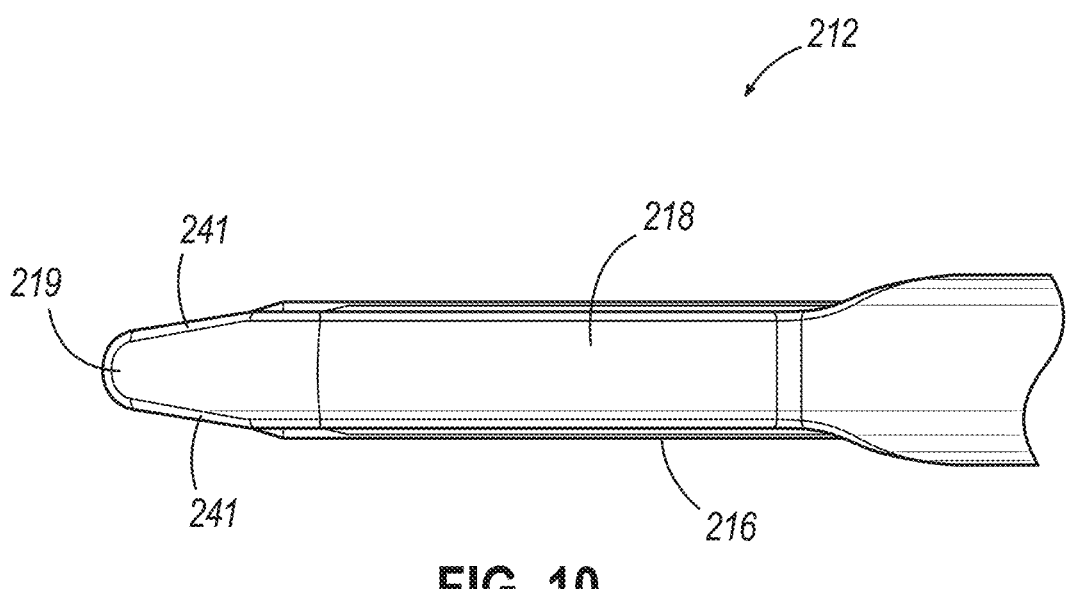
FIG. 10 depicts an enlarged top view of the end effector of FIG. 8.

Anvil jaw 218 as can be seen in FIGS. 8-10 has an elongated shape where the distal portion of anvil jaw 218 angles toward cartridge 237. The distal portion of anvil jaw 218 angles toward cartridge 237 such that the distal most distal tip 219 of anvil jaw 218 extends distally longitudinally further than cartridge 237. Though in some versions, distal tip 219 may extend to a distance longitudinally equal to cartridge 237 or proximal relative to the distal most point on cartridge 237. Furthermore, anvil jaw 218 angles toward cartridge 237 through a gentle slope. As seen best in FIG. 10, anvil jaw 218 includes sides 241 that taper as they approach the distal most distal tip 219 of anvil jaw 218. By way of example, anvil jaw 218 is shaped in FIG. 8 similarly to an inverted ski tip. The angled shape of anvil jaw 218 may provide easier insertion of end effector 212 into a surgical site. For instance, the gentle slope or inverted ski tip shape of anvil jaw 218 may provide an atraumatic tissue deflection surface as anvil jaw 218 contacts or moves through tissue. Such atraumatic tissue deflection may include urging tissue (e.g., a large vessel) proximally into the space between anvil jaw 218 and lower jaw 216 as anvil jaw 218 closes toward lower jaw 216. Once placed into a surgical site, the angled shape of anvil jaw 218 may also provide better maneuverability of end effector 212 and better visibility of the distal end of end effector 212 in relation to anatomical structures at the surgical site. Other suitable variations of anvil jaw 218 will be apparent to one of ordinary skill in the art in view of the teachings herein.

Cartridge 237 is operable to hold staples similar to staples 47 shown in FIG. 4A for driving into tissue. As shown in FIG. 9, the distal end of cartridge 237 has a triangular profile. In particular, the distal end of cartridge 237 includes an upper tapered surface 239 and a lower tapered surface 238. Additionally, the distal end of cartridge 237 includes a tapered side surface 243 on each side. In the present example, each tapered side surface 243 of cartridge 237 generally aligns with the taper presented by sides 241 of anvil jaw 218. Thus, as shown in FIG. 10, side surfaces 243 of cartridge 237 do not extend outwardly from longitudinal axis (LA) of end effector 212 past sides 241 of anvil jaw 218. Upper tapered surface 239 and lower tapered surface 238 lead to the distal most end of cartridge 237. Lower tapered surface 238 defines a sight line 240 such that once end effector 212 is inserted into a surgical site, the user can see along sight line 240. Sight line 240 extends along the edge of lower tapered surface 238. It will be appreciated that the planar shape of lower tapered surface 238 may be operable to allow the user to visualize and/or nearly visualize the distal tip 219 of anvil jaw 218. In particular, sight line 240 intersects longitudinal axis (LA), which extends longitudinally through end effector 212, to form a viewing angle (θ).

Viewing angle (θ) may establish the relative visibility that a user has regarding distal tip 219. In particular, the user can see in front of distal tip 219 along any line of sight that passes through the intersection of sight line 240 and longitudinal axis (LA) within viewing angle (θ). For instance, as viewing angle (θ) increases, the user would have greater visibility of the area immediately in front of distal tip 219 from proximal vantage points; whereas as viewing angle (θ) decreases, the user has less visibility of the area in front of distal tip 219 from proximal vantage points. In some versions, viewing angle (θ) defines an angle greater than 90 degrees. Additionally, in some versions, viewing angle (θ) defines an angle greater than 135 degrees. Other suitable angles for viewing angle (θ) will be apparent to one of ordinary skill in the art in view of the teachings herein. In the illustrated version, the user generally looks along sight line 240 or along some other line of sight within viewing angle (θ), thus, the user has visibility along sight line as well as any area within viewing angle (θ). The underside of distal tip 219 is further slightly rounded to aid in the visibility of the intersection of longitudinal axis (LA) and sight line 240.

When tissue 90 is clamped between a closed cartridge 237 and anvil jaw 218, the user can look along sight line 240 or elsewhere within viewing angle (θ) to see, for instance, precisely where anvil jaw 218 has clamped tissue 90. Furthermore, the user would be able to determine whether the tissue is completely clamped between anvil jaw 218 and cartridge 237 such that tissue does not spill over the end of end effector 212. The user may be able to also visualize the quality of the clamp between anvil jaw 218 and cartridge 237 against tissue 90. It will be appreciated that in some instances, end effector 212 may be rotated before, during, or after clamping tissue 90. As a result, the tapered shape of anvil jaw 218 may also provide more accessible viewing of distal tip 219 or substantially adjacent distal tip 219. The taper of anvil jaw 218 along with lower tapered surface 238 of cartridge 237 may further promote easy insertion of end effector 212 into tissue in an atraumatic manner. Furthermore, it may be easier to fit end effector 212 through a trocar or other devices operable to introduce end effector 212 into a surgical site due to the tapered end of end effector 212. For instance, once distal tip 219 is fit into a trocar, lower tapered surface 238 and the tapered shape of anvil jaw 218 may provide a lead-in, guiding the rest of end effector 212 into the trocar. In view of the teachings herein, those of ordinary skill in the art will further appreciate that visibility and maneuverability can be enhanced by the tapered design for both sides 241 of anvil jaw 218 and each side 243 of cartridge 237.

In addition to the foregoing, end effector 212 and versions of instrument 10 incorporating end effector 212 may be configured and operable in accordance with at least some of the teachings of U.S. Pat. No. 9,186,142, entitled "Surgical Instrument End Effector Articulation Drive with Pinion and Opposing Racks," issued Nov. 17, 2015, the disclosure of which is incorporated by reference herein; U.S. Pat. No. 9,717,497, entitled "Lockout Feature for Movable Cutting Member of Surgical Instrument," issued Aug. 1, 2017, the disclosure of which is incorporated by reference herein; U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; U.S. Pat. No. 9,622,746, entitled "Distal Tip Features for End Effector of Surgical Instrument," issued Apr. 18, 2017, the disclosure of which is incorporated by reference herein; U.S. Pat. No. 10,092,292, entitled "Staple Forming Features for Surgical Stapling Instrument," Oct. 9, 2018, the disclosure of which is incorporated by reference herein; U.S. Pat. No. 9,795,379, entitled "Surgical Instrument with Multi-Diameter Shaft," issued Oct. 24, 2017, the disclosure of which is incorporated by reference herein; and/or U.S. Pat. No. 9,808,248, entitled "Installation Features for Surgical Instrument End Effector Cartridge," issued Nov. 7, 2017, the disclosure of which is incorporated by reference herein. Further modifications that may be incorporated into end effector 212 will be described in greater detail below.

III. End Effectors with Modular Configuration Feature

Figure 11:
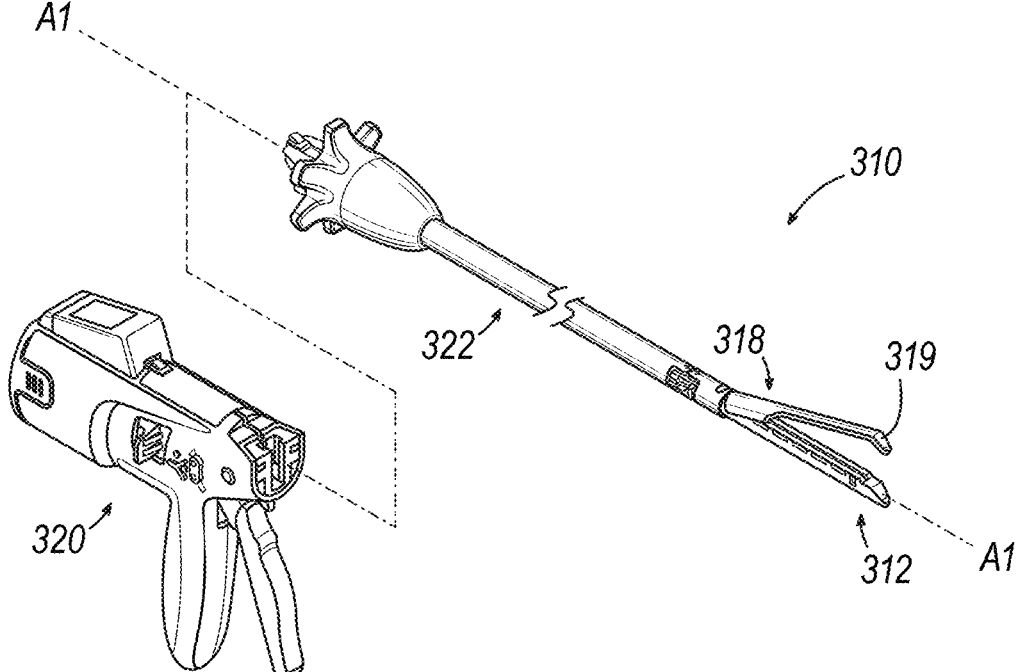
FIG. 11 depicts a perspective view of an example of a surgical stapling instrument having a modular handle and shaft, and an end effector with a curved elastically deformable tip section.

FIG. 11 shows another example of an instrument 310 configured as a surgical stapler. Instrument 310 includes a handle portion 320 and a shaft 322. Instrument 310 has a modular configuration such that shaft 322 is selectively removable from, and attachable to, handle portion 320. Instrument 310 is configured similarly to instrument 10 such that the operability and use of instrument 310 is the same as described above for instrument 10 with the added feature of instrument 310 being a modular configuration. With its modular configuration, instrument 310 provides a way to change the end effector. Such a change in the end effector may be made to replace an otherwise worn end effector, or to provide for a different end effector configuration based on the procedure or user preference. In addition to or in lieu of the foregoing, features operable for providing the modular configuration of instrument 310 may be configured in accordance with at least some of the teachings of U.S. Pat. No. 10,182,813, entitled "Surgical Stapling Instrument with Shaft Release, Powered Firing, and Powered Articulation," issued Jan. 22, 2019, the disclosure of which is incorporated by reference herein. Other suitable components, features, and configurations for providing instrument 310 with a modular configuration will be apparent to those of ordinary skill in the art in view of the teachings herein. Moreover, it will be understood by those of ordinary skill in the art in view of the teachings herein, that instrument 10 may be modified to incorporate a modular configuration as shown and described with respect to instrument 310 or other instruments incorporated by reference herein.

In the illustrated example of FIG. 11, instrument 310 includes an end effector 312 having an anvil jaw 318 that has an angled distal tip 319.

It will be appreciated that end effector 312 may be used in place of end effector 12 shown in FIG. 1. In some versions, end effector 312 may be integrally formed with shaft 22 or alternatively may be separately formed and then combined. In some versions, end effector 312 may be provided for use in robotic systems. In such robotic systems, modular shaft 322 having end effector 312 may be attachable to a portion of the robotic system for use such that handle portion 320 is replaced by components of the robotic system. Still in other examples, end effector 312 may be adapted for use with a robotic system in a manner where end effector 312 connects with the robotic system without necessarily connecting the entire modular shaft 322. In view of the teachings herein, other ways to incorporate an end effector having an angled elastically deformable anvil tip into a user operated or robotic operated instrument will be apparent to those of ordinary skill in the art.

IV. Accessory Device to Sense And Communicate Tissue Force And Thickness

Augmented sensing, feedback, and connectivity are desired for both robotic and handheld instruments used in both laparoscopic and open surgeries. The surgical stapling features of the present disclosure seek to enhance preoperative planning, surgical performance, therapeutic support, and training to improve patient outcomes and reduce harm. In particular, the surgical stapling features of the present disclosure augment and enhance a user's, e.g., a surgeon or a robotic system, perception of a tissue by providing feedback to help inform intraoperative decisions based on data sensed, obtained, and transmitted by an accessory sensor.

When the jaws of a surgical stapler are clamped on a tissue, i.e., when the jaws of the surgical stapler constrict, compress, or press the tissue and the tissue sensor together so as to hold the tissue and the tissue sensor, it may be difficult for a user to determine various characteristics and properties of the tissue such as compressibility and compressed thickness, property variability (ability to stretch and shape), and biphasic (both liquid and solid characteristics), before performing a firing stroke through the tissue and stapling through tissue on each side of the cut line produced by the firing stroke. Knowledge of these characteristics and properties of the tissue may be desired by the user to properly select, for example, which force to use for the transection of the tissue, which type of cartridge, and/or which height of the staples to select before transection of the tissue. Without fore knowledge of these characteristics of the tissue, it may be uncertain whether the selected cartridge is proper for the targeted tissue. For example, if the type of the selected cartridge and the height of the selected staples do not match the targeted compressed thickness of the tissue, the sealing outcome may not be optimal.

The disclosed embodiments relate to an accessory sensor, i.e., a tissue sensor or a tissue sensor system, used with the surgical stapling instrument to sense tissue characteristics and to provide accurate tissue measurements to the user prior to the firing stroke through the tissue. The accessory or tissue sensor may sense and wirelessly communicate tissue characteristics such as, for example, tissue force, thickness, and/or position measurements. The accessory sensor may include force, proximity, and location sensors arranged in an array, a power source such as a battery, necessary electronics, and a transmitter disposed in a flexible substrate. The transmitter enables connection of the accessory sensor to other equipment, e.g., a computer disposed in an operating room. The accessory sensor may be configured as a thin film accessory. The thin film nature of the accessory sensor and the flexibility of the substrate may allow the tissue sensor to conform or deform with an object or structure on which the sensor is installed or disposed. The conformability of the sensor may be useful in connection with monitoring tissues where surfaces are curved and complex. Further, the thin film nature of the accessory sensor enables the accessory sensor to sense and measure the tissue characteristics without impacting or otherwise contributing to that measurement. In some instances, if the accessory sensor is too thick, it may itself result in compressing the tissue more than would be compressed by only the surgical stapling instrument itself with a regular cartridge in place. The tissue sensor may be configured to take the thickness of the tissue and tissue sensor into account before measuring the tissue characteristics.

The accessory sensor enables measurement and communication of tissue force and thickness before transection (pre-transection) of the tissue. The accessory sensor may be used with many other different types of devices, tools, and instruments. The accessory sensor may be easily inserted, removed, or pushed aside before transection of the tissue. The accessory sensor provides an efficient mechanism to solve the problem of sensing and communicating tissue characteristics without having to rely on the surgical stapling instrument alone to perform these tasks, such as having the disclosed tissue sensor system miniaturized to fit within a normal cartridge-sized device to be accommodated within the surgical stapling instrument. Specifically, as noted above, the accessory sensor provides several enhancements such as augmented sensing, feedback, and connectivity. Further, using the tissue sensor provides an improved ease of use, e.g. the tissue sensor may be larger than the dimensions of the jaws of the surgical stapling instrument so that the tissue sensor may be disposed over a wider area of tissue and then more easily clamped onto because the user does not have to try to grab the tissue with precision. In some embodiments, the tissue sensor may allow the user to lay the tissue sensor over a large area of the tissue and then move the tissue sensor around to test different locations. In some embodiments, when the end effector includes self-marking devices described below, having the ability to lay the tissue sensor over a large area of the tissue may allow the user to identify and mark different areas of the tissue.

In particular, the disclosed embodiments relate to a tissue sensor that is configured to be used in conjunction with a surgical stapling instrument (e.g., a surgical stapler), and a tissue of a body. In some embodiments, the tissue sensor may transmit, via a wireless or wired medium, tissue measurements along jaws of the surgical stapler clamped on the tissue to a processor of a computer, e.g., an operating room computer, located outside of the body.

Figure 12:
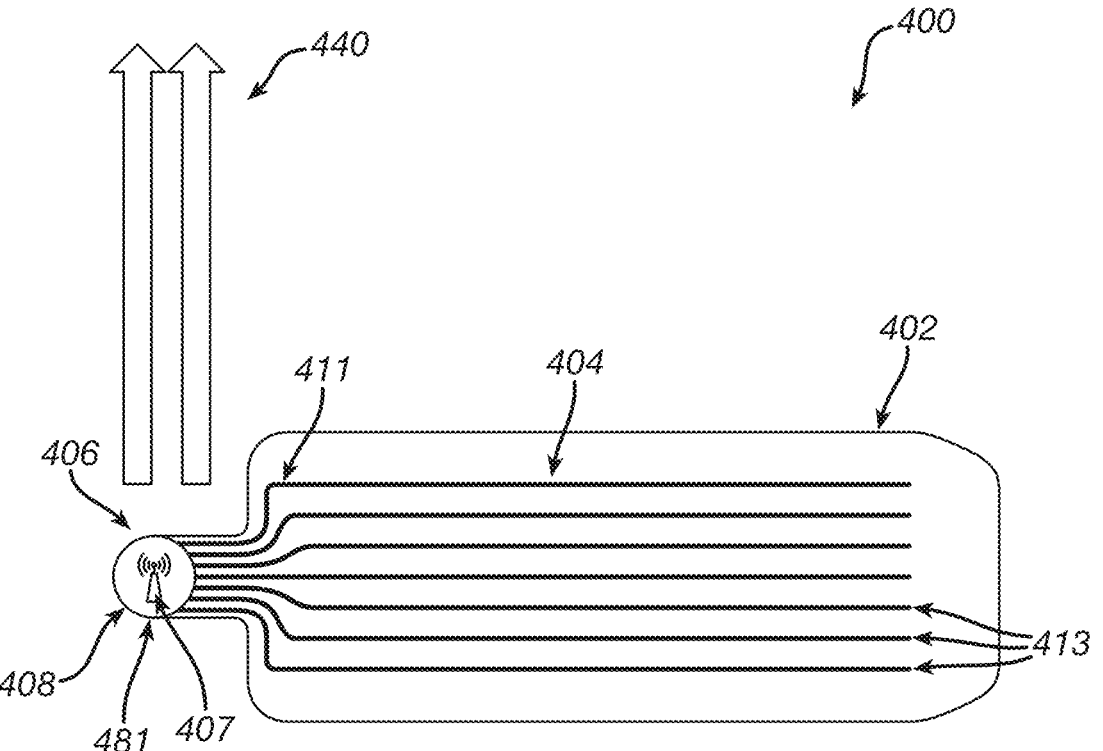
FIG. 12 depicts a top view of a tissue sensor according to one embodiment.
Figure 13:
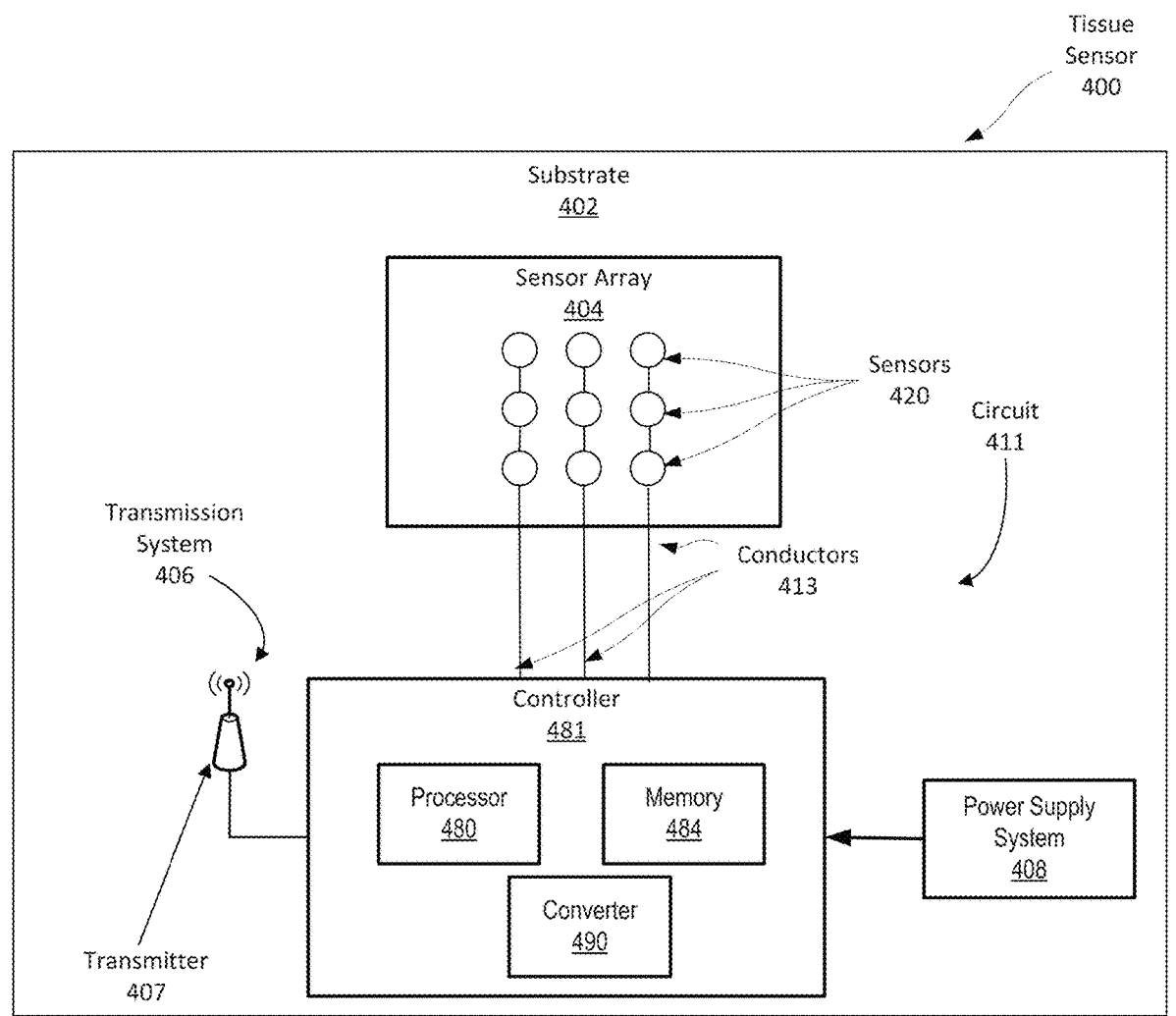
FIG. 13 depicts a tissue sensor according to one embodiment.

FIGS. 12 and 13 depict an example of a tissue sensor/ tissue system 400. The tissue sensor 400 (also shown in FIG. 16) includes a flexible substrate or structure 402, a sensor array 404, and a controller 481. The tissue sensor 400 may further include a transmission system 406 (including a transmitter 407) and a power supply system or power source 408.

In some embodiments, the tissue sensor 400 may be configured to be disposed of after a single use or to be reusable, i.e., to be used multiple times. In particular, the tissue sensor 400 may be reconditioned for reuse after at least one use or may be reconditioned and reused multiple times for more than one sensing operation in the same patient and/or on multiple patients. Reconditioning may include any combination of the steps of disassembly of the tissue sensor 400, followed by cleaning and sterilization (further described below) or replacement of particular pieces, and subsequent reassembly. In particular, in some embodiments, the tissue sensor 400 may be disassembled, and any number of the particular pieces or parts of the tissue sensor 400 may be selectively replaced or removed in any combination. Upon cleaning and/or replacement of particular parts, the tissue sensor 400 may be reassembled for subsequent use either at a reconditioning facility, or by a user immediately prior to a procedure. Reconditioning of the tissue sensor 400 may utilize a variety of techniques for disassembly, cleaning/replacement, and reassembly. Therefore, the tissue sensor 400 may include materials that can withstand repeated reconditioning, including the use of chemicals.

In some embodiments, the user may insert the tissue sensor 400 into a body, target a tissue, dispose the tissue sensor 400 on the targeted tissue, clamp the tissue sensor 400, perform a sensing operation including transmitting feedback data (i.e., sensed data) to the user, and either leave the tissue sensor 400 in the body or remove the tissue sensor 400 from the body. Based on the feedback/sensed data received from the tissue sensor 400, the user may switch out the staple cartridge and complete the firing. The user may then target another tissue, dispose the tissue sensor 400 on the other targeted tissue, and complete a next sensing operation. In some embodiments, the tissue sensor 400 may be used multiple times in a single procedure or may be removed after one instance of use. Before ending the procedure, the tissue sensor 400 may be removed from the patient.

In some embodiments, the tissue sensor 400 may be configured to be separately inserted, e.g., by the user when performing open surgery procedures. In some embodiments, the tissue sensor 400 may be configured to be rolled up so that it can fit through a trocar. In some embodiments, the tissue sensor 400 may be attached to the surgical stapler and may be inserted and removed via the end effector of the surgical stapler.

Figure 16:
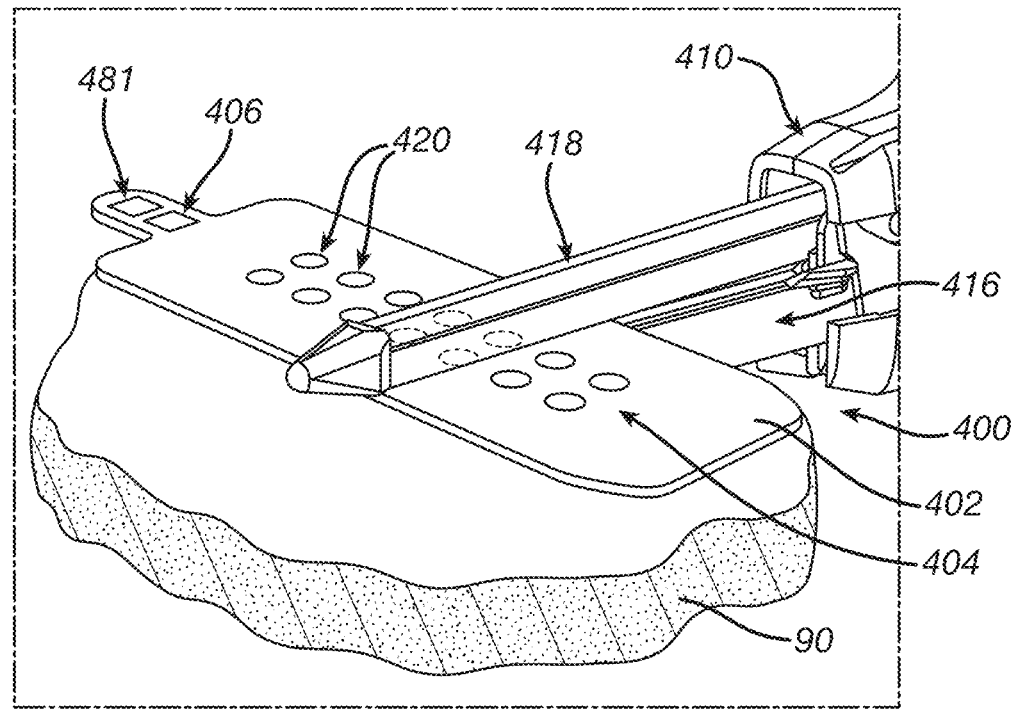
FIG. 16 depicts a perspective view of a tissue sensor disposed between jaws of a surgical stapler and a tissue according to one embodiment.
Figure 17:
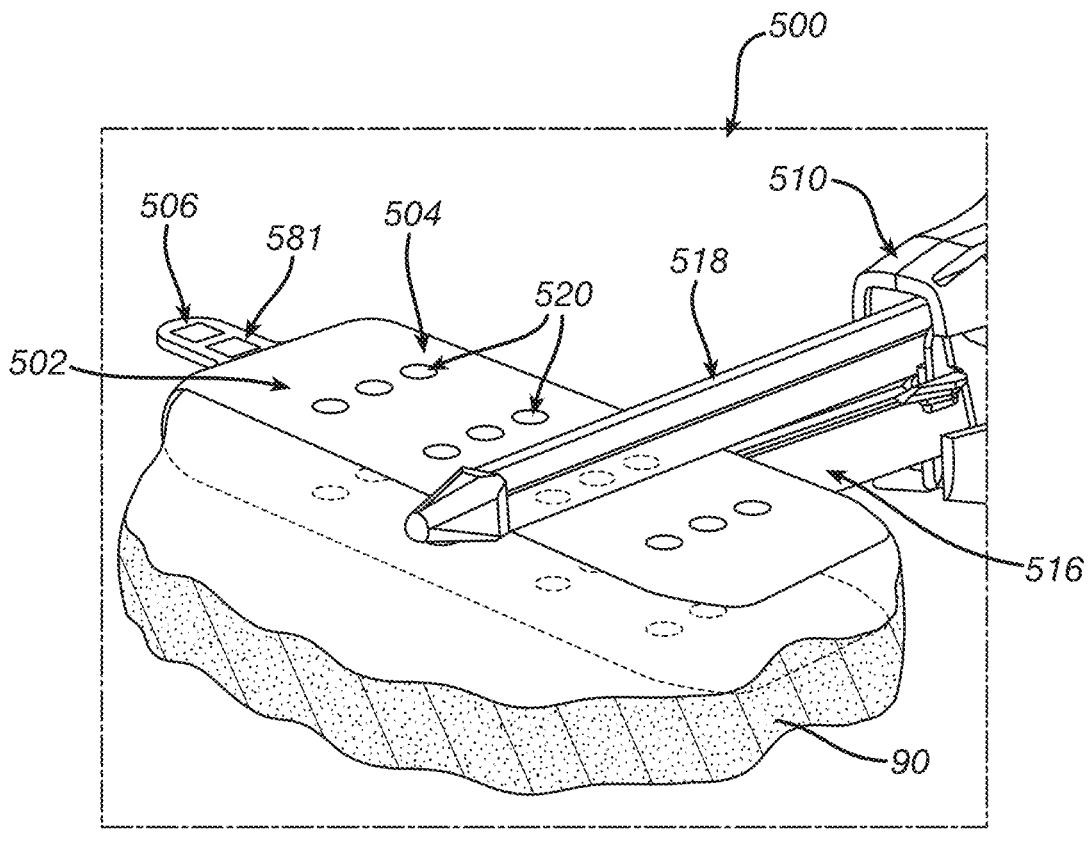
FIG. 17 depicts a perspective view of an alternate version of a tissue sensor disposed between jaws of a surgical stapler and a tissue according to one embodiment.

The flexible substrate 402 is configured to be flexible and may be applied to various types of surfaces. For example, the flexible structure 402 may be used in various monitoring contexts in which an object, for example, a tissue of a body, expands and contracts. As noted above, the flexibility of the flexible substrate 402 enables the tissue sensor 400 to deform with the surface on which the tissue sensor 400 is applied or disposed. The flexible substrate 402 may be further configured to be disposed between two surfaces. As shown in FIG. 16, the flexible substrate 402 is configured to be disposed between a tissue 90 and a surgical stapler 410. In particular, the flexible substrate 402 is configured to be disposed between the tissue 90 and either the first jaw 418 or the second jaw 416 of the surgical stapler 410. In some embodiments, as shown in FIG. 17, the flexible substrate 402 is configured to be wrapped around and be disposed on opposite surfaces of the tissue 90 such that the flexible substrate 402 is disposed between the tissue 90 and the jaws (e.g., the first jaw 418 and the second jaw 416) of the surgical stapler 410. In some embodiments, the flexible substrate 402 may include a thin flat film. In some embodiments, the flexible substrate 402 may include a sensor pad. In some embodiments, the flexible substrate 402 may include biocompatible materials, i.e., materials that do not produce a toxic or immune response within the human body, such as thin plastic, rubber, silicone, plastic composite film, polyurethane, piezoelectric film, and the like. In some embodiments, the thickness of the flexible substrate 402 may be equal to or less than 0.005". In some embodiments, the flexible substrate 402 may be configured to be longer than it is wide. In some embodiments, the flexible substrate 402 may be configured to have a width that is wider than at least the staple cartridge.

The sensor array 404 includes sensors, i.e., a plurality of sensors 420, 520, or 620 (shown, for example, in FIGS. 13, 16, 17, and 19), disposed in an array on the flexible substrate 402. The sensor array 404 is configured to sense or detect a parameter, e.g., one or more parameters of an object, such as the tissue 90, in contact therewith, and generate a signal(s), e.g., one or more signals, or a plurality of signals, indicative thereof in response to a force, such as a clamping force, that is applied by the surgical stapler 410 to clamp the tissue 90 and the tissue sensor 400 together. In other words, the surgical stapler 410 is configured to apply force to constrict, compress, or press the tissue 90 and the tissue sensor 400 together so as to hold the tissue 90 and the tissue sensor 400 together.

In some embodiments, the plurality of sensors 420 may be arranged in different configurations, e.g., at regular intervals or at irregular intervals on the flexible substrate 402. In some embodiments, the jaws of the surgical stapler 410 may be hinged at the proximal end of the surgical stapler 410 and the jaws may not deliver even pressure as they close. The arrangement of the plurality of sensors 420 may be configured to account for the difference due to the unevenness of the pressure imparted by the jaws on the tissue 90.

In some embodiments, the sensor array 404 may be configured as thin film sensors. In some embodiments, the sensor array 404 may include force sensors, pressure sensors, location sensors, humidity and moisture content sensors, oxygen saturation sensors, temperature sensors, media PH sensors, and glucose concentration sensors, or combinations thereof disposed in an array. In other words, the sensor array 404 may comprise any suitable sensors for sensing, detecting, and measuring one or more parameters of an object in contact with the sensor array 404. For example, in various embodiments, the sensor array 404 may comprise magnetic sensors, such as Hall effect sensors and magnets, strain gauges, pressure sensors, inductive sensors, such as eddy current sensors, resistive sensors, capacitive sensors, optical sensors, impedance sensors, and/or any other suitable sensors. In some embodiments, the sensor array 404 may include, for example, a single continuous pressure sensing film and/or paper and/or an array of pressure sensing films. The sensor array 404 may be disposed between two surfaces to measure at least force, interface pressure, location, position, or combinations thereof.

The controller 481 is coupled with the sensor array 404 and is disposed on the flexible substrate 402. In particular, the plurality of sensors 420 may be electrically connected (e.g., wired) to the controller 481 via conductors 413 (e.g. wires). The controller 481 may be configured to receive the signals, e.g., analog signals, from the sensor array 404 and process the signals to derive or determine characteristics of the tissue 90, the surgical stapler 410, or other substances, in contact with the plurality of sensors 420. In particular, the controller 481 is configured to receive the plurality of signals from the sensor array 404, process the plurality of signals to determine a measurement of the parameter based on the plurality of processed signals, and provide an indication of the measurement of the parameter to a user of the surgical stapler 410 to enable the user to make further decisions based on the measurement of the parameter.

In certain instances, as shown in FIG. 13, the controller 481 may include a microprocessor 480 ("processor") and one or more computer readable mediums or memory units 484 ("memory") coupled therewith. In certain instances, the memory 484 may store various program instructions, which when executed, may cause the processor 480 to perform a plurality of functions and/or calculations described herein.

In certain instances, the controller 481 may be at least partially digital. In some examples, the controller 481 may be implemented utilizing dedicated hardware, such as one or more of discrete components, an integrated circuit, an application-specific integrated circuit (ASIC), a programmable logic device (PLD), a processor executing firmware instructions, a processor executing software instructions, or any combination thereof. When implemented utilizing a processor executing software or firmware instructions, the software or firmware instructions may be stored in any suitable computer readable memory such as on a magnetic disk, an optical disk, or other storage medium, etc. The software or firmware instructions may include machine readable instructions that, when executed by one or more processors, cause the one or more processors to perform various acts related including detecting tissue characteristics, clamping force, and location conditions based on the signals including data indicative of measurements obtained using the plurality of sensors 420, to provide indications to a user of the surgical stapler 410, etc.

In some implementations, the controller 481 may include one or more digital to analog converters (DACs) and one or more analog to digital converters (ADCs) 490 configured to convert signals between analog signals suitable for use with the sensor circuit 411 and digital signals used with digital circuitry of the controller 481.

The transmission system 406 may be coupled with the controller 481 and may be disposed on the flexible substrate 402. The transmission system 406 may include a communication interface that may utilize any suitable communications medium, such as, for example, wired or wireless communications systems, e.g., Wi-Fi, Bluetooth, and near-field communication (NFC). In particular, the transmission system 406 may include a transmitter 407 coupled with the sensor array 404. The transmitter 407 communicates with the sensor array 404 and/or the controller 481 and may transmit, via a wireless or wired medium, a plurality of processed signals 440 indicative of different data sensed by the sensor array 404 to different devices, such as other processors or controllers.

In some embodiments, the signals may include analog signals indicative of the parameter and the tissue sensor 400 may transmit the analog signals to an ADC 490 to convert the analog signals to digital signals including data indicative thereof, i.e., data indicative of the sensed parameter which can be used by the controller 481 to derive and determine data including but not limited to characteristics of the tissue 90, force applied by the surgical stapler 410 to the tissue sensor 400 and the tissue 90, and location of the surgical stapler 410 in the tissue sensor 400. In some embodiments a sensor of the plurality of sensors 420 and the ADC 490 may be co-located or the sensor 420 may be remote from the ADC 490. In some embodiments, the plurality of sensors 420 may be coupled with a single ADC 490 disposed on the flexible substrate 402. In some embodiments, as mentioned above, the controller 481 may include an ADC 490. In some embodiments, the controller 481 may be coupled with the ADC 490. The ADC 490 may receive and convert the analog signals from more than one sensor 420 and may transmit the converted digital signals to the controller 481 for further processing. In some embodiments, as shown in FIG. 13, the controller 481 may include the ADC 490 and may receive, convert, and process the analog signals. In some embodiments, the ADC 490 may be coupled with the transmitter 407 which may include a radio that communicates the converted signals including data indicative of the sensed parameter to a receiver, e.g., a processor of a computer, which may then process the converted digital signals.

In some embodiments, the data indicative of the sensed parameter may also be encoded and/or compressed prior to transmission, particularly when a low bandwidth and/or low power communication medium is used.

In some embodiments, the transmitter 407 may transmit the plurality of signals 440 to computers or devices, e.g., the surgical stapler 410, and/or a processor of a computer, located inside and/or outside of the patient's body in which the tissue sensor 400 is being used (e.g., computers located in an operating room). In some embodiments the transmitter 407 may communicate real time information via other equipment and provide information and/or alerts to the user.

In particular, as mentioned above, the transmitter 407 may be coupled with the controller 481 and disposed on the flexible substrate 402. The transmitter 407 may be configured to transmit (wired or wirelessly) the plurality of processed signals 440 to a processor of a computer such as the processor 482. The processor may be configured to cause the measurement of the parameter to be displayed on a display coupled with the computer, or a display disposed on the handle of the surgical stapler 410 and/or configured to communicate the measurement by audible tone via speakers coupled with the computer or the surgical stapler 410, or by a non-audible means such as vibration (haptic feedback) in the surgical stapler 410.

FIG. 13 depicts a tissue sensor 400 including a control circuit 411, shown in FIG. 12, configured to detect, measure, and transmit data indicative of characteristics of the surgical stapler 410 and the tissue 90. The control circuit 411 includes the sensor array 404, the controller 481, the transmission system 406 the power supply 408, and the conductors 413 and provides electrical connection between the sensor array 404, the controller 481, the transmission system 406, and the power supply system 408. The control circuit 411 may enable the transmission of the signals between the sensor array 404 and the controller 481 via the conductors 413. The controller 481 may be configured to control one or more operations of the tissue sensor 400.

The power supply system 408 may be disposed on the flexible substrate 402. The power supply system 408 may be configured to supply power to the sensor array 404, the transmission system 406 and the controller 481 via an electrical connection, for example. The power supply system 408 may include a power source such as a battery, capacitor, or a near field or inductive power source. In certain instances, the battery (or "battery pack" or "power pack") may be a Li ion battery, for example. A number of battery cells connected in series may be used as the power source 408 as well. In certain instances, the power source 408 may be replaceable and/or rechargeable, for example. In other examples, such as open surgeries, the flexible substrate 402 may be connected to an electrical outlet, external battery or other wired power source via a wire or power cord.

In some embodiments, a user may desire to determine, for example, various characteristics of a surgical site, e.g., a tissue 90 in the body of the patient such as compressibility and compressed tissue thickness, moisture content, electrical conductivity, and the like before performing a firing stroke and stapling through the tissue.

Figure 14:
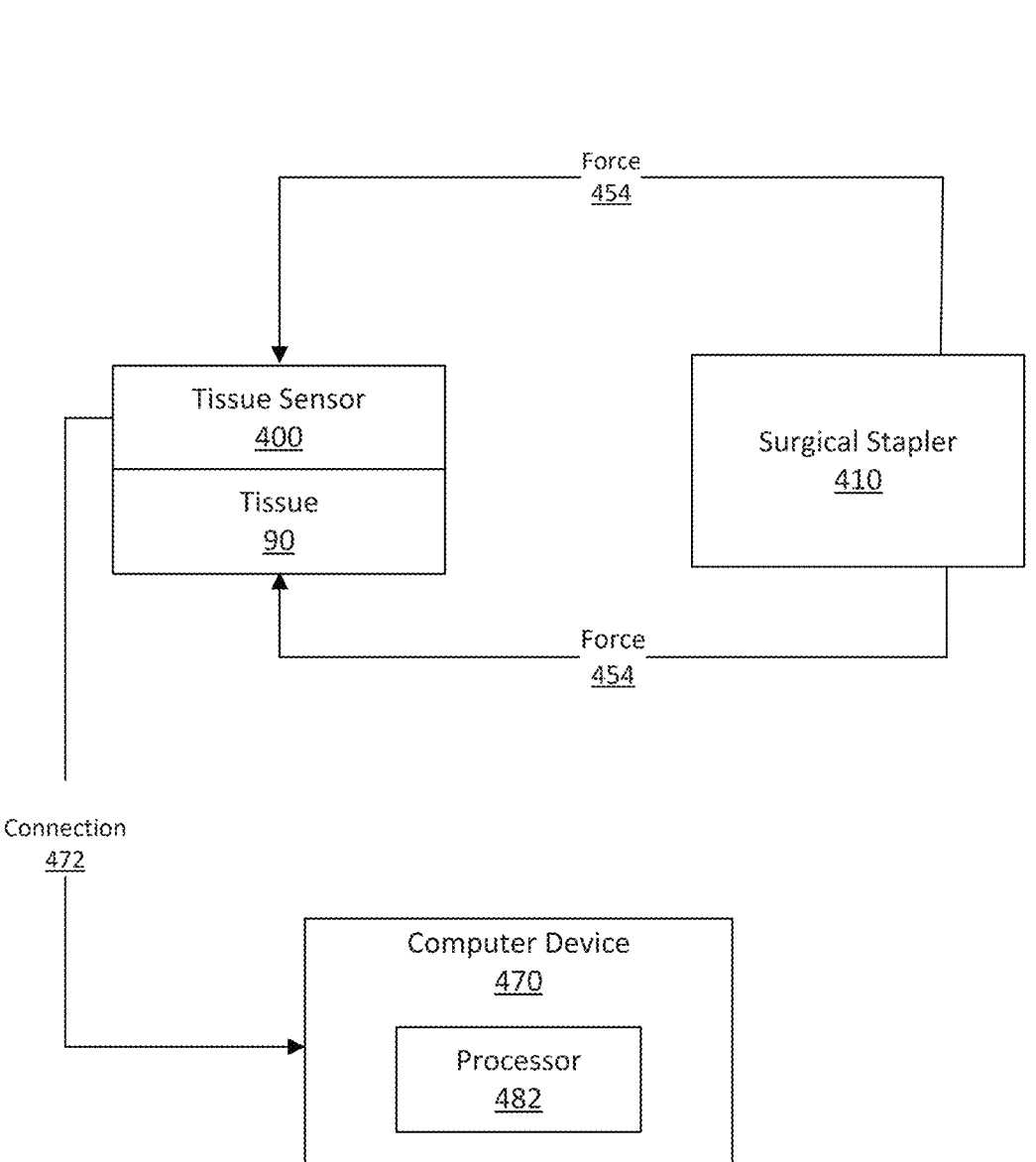
FIG. 14 depicts a diagram of a wireless tissue sensor detector system according to one embodiment.

FIG. 14 illustrates a diagram of a tissue sensor system 450 configured to be used in conjunction with a surgical stapler 410 and the tissue 90 and to determine various characteristics of the tissue 90 and/or the surgical stapler 410, according to one embodiment.

In some embodiments, the tissue sensor system 450 includes a tissue sensor 400, a surgical stapler 410, and a computer device 470. The tissue sensor 400 may be disposed between jaws of the surgical stapler 410 and the tissue 90.

The surgical stapler 410 may apply force 454 and clamp the tissue sensor 400 and the tissue 90 together. The tissue sensor 400 may detect or sense the applied force 454, generate a plurality of signals, process the plurality of signals, and send a plurality of processed signals 440 including data indicative of different data sensed by the tissue sensor 400 via a connection 472 to a processor 482 of a computer device 470. The connection 472 may include a wireless or a wired connection. The computer device 470 may be disposed outside of the body of the patient, e.g., in an operating room.

FIG. 15 illustrates a diagram of a tissue sensor system 460 that enables transmission of a plurality of signals 440. The tissue sensor system 460 is configured to overcome transmission problems, such as due to wireless interference caused by the human body during some procedures, including both laparoscopic and open surgeries.

In some embodiments, the surgical stapler 410 may be inserted with the tissue sensor 400 through a trocar cannula or an incision to a surgical site, e.g., a tissue 90, in the body of a patient 452 for performing surgical procedures such as endoscopy or laparoscopy.

In one embodiment, the surgical stapler 410 may include a handle portion 421 connected to a shaft 422 coupled with an end effector 412 extending distally from the shaft 422. As previously stated, the surgical stapler 410 may be used for laparoscopic and open surgical procedures.

To determine various characteristics of the tissue 90, the end effector 412 may be inserted with the tissue sensor 400 inside the body of the patient 452. In one example, the tissue sensor 400 may be rolled up around the end effector 412 as the end effector 412 is inserted into the body. The tissue sensor 400 may be disposed laying on a surface of the tissue 90, e.g., on top or bottom of the tissue 90, by the end effector 412 (e.g., unrolled and positioned on top of the tissue). In some examples, as discussed above, the tissue sensor 400 may be placed on the desired tissue by the user (e.g., surgeon or robotic system), such as during open surgical procedures. In other examples, the tissue sensor 400 may be introduced to the body of a patient through a natural orifice or port. In particular, the tissue sensor 400 may be disposed via an instrument, e.g., a laparoscopic grasper, via another port. In other examples, the tissue sensor 400 may be attached to the end of a trocar and disposed laying on a surface of the tissue 90 when the trocar is installed into the patient. In other examples, the tissue sensor 400 may be attached to a suture outside the patient, then disposed onto the tissue 90 via the act of suturing. In other examples, the tissue sensor 400 may include two pieces and be easily attached once the tissue sensor 400 is inside the body since it is easier to fit through a trocar.

In some instances, during open or laparoscopic procedures, upon the end effector 412 clamping the tissue 90 and the tissue sensor 400 together, the tissue sensor system 460 may have difficulty transmitting signals due to interference (e.g., the walls of the body of the patient 452, the distance between the tissue sensor 400 and the computer device 470, and the like). In some of these situations, the result may be that the plurality of signals 440 cannot be transmitted via the wireless connection 472 to the computer device 470.

To alleviate these potential interference issues, the tissue sensor 400 may be configured to enable the transmission of the plurality of signals 440 by wirelessly transmitting, via a first wireless connection 474 having a short signal transmission distance, e.g., less than 30 cm, the plurality of signals 440 to a signal relay 485 disposed in the distal end of the end effector 412. The signal relay 485 then routes the plurality of signals 440 to a router system 487 disposed in a proximal end of the shaft 422 disposed outside of the body of the patient 452 via a wired connection 478, which solves the wireless transmission problems mentioned above. The router system 487 then transmits, either via a wireless or wired medium, the plurality of signals 440 to the processor 482 of the computer device 470 located outside of the body of the patient 452. In another example, the processor 482 and the computer device 470 may be integrated in the handle of the surgical stapler 410 and the surgical stapler 410 may be configured to display data indicative of the plurality of signals 440.

FIG. 16 illustrates one embodiment of the tissue sensor 400 disposed between jaws of a surgical stapling instrument 410 (e.g., a surgical stapler 410) and the tissue 90. The tissue sensor 400 is configured to be an accessory to the surgical stapler 410. Specifically, the tissue sensor 400 is configured to be used with the surgical stapler 410 and the tissue 90. In particular, the tissue sensor 400 is configured to be disposed between the tissue 90 and jaws of the surgical stapler 410. In some embodiments, the tissue sensor 400 may be configured to be disposed laying on a surface of the tissue 90, e.g., on top of the tissue 90 or at the bottom of the tissue 90, such that the tissue sensor 400 is between the tissue 90 and the surgical stapler 410. In some embodiments, the tissue sensor 400 is configured to be wrapped around the tissue 90, such that the tissue sensor 400 is on both sides (i.e., top and bottom) of the tissue 90, as shown in FIG. 17.

In some embodiments, the surgical stapler 410 may include a first jaw 418 (e.g., an anvil jaw) pivotably coupled at a proximal end thereof with a second jaw 416 (e.g., a lower jaw). The tissue sensor 400 may be disposed between the first jaw 418 and the tissue 90 or between the second jaw 416 and the tissue 90.

The surgical stapler 10 is configured to be actuated to clamp the tissue 90 and the tissue sensor 400 together. In particular, the first jaw 418 and the second jaw 416 are configured to be movable relative to each other to grasp the tissue 90 and the tissue sensor 400 therebetween. The surgical stapler 10 is configured to be actuated to pivot one of the first 418 or second jaw 416 relative to the other of the first 418 or second jaw 416 to clamp the tissue 90 and the tissue sensor 400 together.

The sensor array 404 may include any suitable sensors for detecting and sensing a parameter or one or more parameters. The parameter may be indicative of characteristics of the tissue 90, a clamping condition, a location condition, or combinations thereof. In particular, the sensor array 404 is configured to sense a parameter, in response to a force 454, e.g., a clamping force, which is a force applied by the actuation of the surgical stapler 410 to clamp the tissue 90 and the tissue sensor 400 together. The sensor array 404 is also configured to generate a signal thereof (e.g., of the sensed parameter, such as force/pressure), and transmit the signal to the controller 481. The controller 481 may be configured to, based on the received signals, determine different characteristics of the tissue 90 such as, for example, compressibility and compressed thickness, property variability, and biphasic characteristics of the tissue 90. The controller 481 may further determine or derive characteristics of the surgical stapler 410 such as the force 454 applied by the surgical stapler 410 to the tissue 90 or the location of the surgical stapler on the tissue sensor 400.

In particular, the sensor array 404 may be configured to generate a plurality of signals (e.g., analog signals) indicative of a parameter (or parameters) and to transmit the analog signals to different devices. Specifically, the sensor array 404 may be electrically connected to the controller 481 and may transmit the analog signals to the controller 481 which may convert and process the analog signals to determine a measurement of a parameter. The sensor array 404 may transmit the processed digital signals to the transmission system 406 which may transmit the digital signals to different devices such as the surgical stapler 410. In some embodiments, the operation of the surgical stapler 410 may be adjusted by the user as a function of the measurement of the parameter.

In some embodiments, the tissue 90 may refer to a tissue of a body of a patient and the different devices may include the surgical stapler 410, and/or computers located outside of the body of the patient, and the like.

The clamping condition may be indicative of an amount of pressure that is exerted by the surgical stapler 410 on the clamped tissue 90 and the tissue sensor 400.

The controller 481 may be configured to adjust the measurement of the parameter based on the processed signals 440 as the tissue 90 is being clamped over time. The adjusted measurement may dynamically vary based on the clamping of the tissue 90. A current value of the adjusted measurement may be indicative of tissue characteristics, clamping positioning, or tissue characteristics and clamping positioning at a time of measurement.

The controller 481 may be configured to, based on the processed signals 440, determine a measurement of the clamping force applied by the surgical stapler 410 to clamp the tissue 90 and the tissue sensor 400 together. The controller 481 may also be configured to, based on the processed signals 440, determine various characteristics of the tissue 90.

In some embodiments, the surgical stapler 410 may be clamped by a user and the user may wait for the tissue 90 to stabilize before the user reads the measurements (in one example, this wait time may be 15 seconds, but in other examples the wait time may be shorter or longer). Therefore, in one implementation, as the plurality of sensors 420 detect pressure, the tissue sensor 400 may continue to transmit the processed signals 440 and send its readings and measurements. Therefore, the user may determine how long to wait for those readings to stabilize, stop fluctuating, and the like. The controller 481 of the tissue sensor 400 may be configured to determine that the readings are changing/fluctuating. Therefore, the controller 481 may wait, for example, until the readings stabilize, within a range or margin, or when the rate of change falls below a threshold, before sending a final reading via the transmitter 407.

In some embodiments, the plurality of sensors 420 may include a plurality of pressure sensors disposed in the flexible substrate 402. Each of the pressure sensors 420 is configured to detect and sense a mechanical force, e.g., compression or pressure, as input in response to the clamping of the tissue 90 and the tissue sensor 400 by the first 418 and second jaw 416. The plurality of pressure sensors are configured to convert the detected pressure into an electrical output signal, e.g., impedance, that can be measured. As the force applied increases, the electrical signal changes proportionally. The detected electrical output signal (based on the detected pressure in response to the force applied by the jaws of the surgical stapler 410) may be indicative of the thickness and/or fullness of the clamped tissue 90. The plurality of sensors 420 may generate a plurality of signals indicative of the detected pressure.

In some embodiments, the flexible substrate 402, including the plurality of sensors 420, may be disposed on top of the tissue 90 or at the bottom of the tissue 90 or both (e.g., wrapped around the tissue 90). The plurality of sensors 420 are configured to sense a parameter in response to a force exerted by the first jaw 418 and the second jaw 416 on the tissue 90. In some embodiments, the plurality of sensors 420 are configured to be individually readable or addressable by the controller 481. The plurality of sensors 420 may be grouped in zones. In some embodiments, the plurality of sensors 420 may comprise an array of pressure sensors, a single continuous pressure sensing film and/or an array of pressure sensing films. The controller 481 may be configured to determine variations in the measured pressure at different locations between the proximal and distal ends of the first jaw 418 and/or the second jaw 416 of the surgical stapler 410.

The plurality of generated signals 440 may be provided to a processor 482 which applies one or more algorithms based on the input from the plurality of sensors 420 to determine one or more parameters of the surgical stapler 410 and/or the tissue 90. For example, in one embodiment comprising a plurality of pressure sensors, either the processor 480 or the processor 482 of the computer device 470 is configured to apply an algorithm to quantitatively compare the output of the plurality of sensors 420 with respect to each other and with respect to a predetermined threshold to determine how many outputs are valid and how many outputs are needed for an accurate measurement. In some embodiments a predetermined threshold testing may be done to establish expected values for using the tissue sensor 400 on the tissue 90 with the surgical stapler 410. If the measurement taken by the tissue sensor 400 falls outside of that expected range, the measurement may be considered invalid. In another example, an output may be determined to be valid when there is any differential between a steady state sensing and a real-time sensing. For example, if a measurement differential=0, then the output is determined to be valid. When the measurement differential>0 or <0, then the output is determined to be invalid. In some embodiments, the tissue sensor 400 may be compared to other sensors in certain dimensions and examined for unlikely scenarios. For example, the plurality of sensors 420 may be disposed in a line in a configuration in which minimal spacing is included between them. If a first sensor 420 generates a high reading, a second sensor 420 generates a low reading, and a third and fourth sensors 420 both generate a higher reading, the low reading generated by the second sensor 420 may be invalid.

The parameters measured by the sensor array 404 may be indicative of different characteristics of the tissue 90, a clamping condition, a location condition of the surgical stapler 410, or combinations thereof. In particular, the clamping condition may be indicative of a pressure exerted by the surgical stapler 410, e.g., by the first 418 and second jaws 416, on the tissue 90 clamped between the first jaw 418 and the tissue sensor 400 or between the tissue sensor 400 and the second jaw 416. In one example, the clamping condition may simply indicate whether the tissue 90 is clamped or not. The clamping condition may also be indicative of a force applied to actuate the surgical stapler 410, e.g., the first 418 and second jaws 416, to clamp the tissue 90 and the tissue sensor 400 together. The location condition may be indicative, when the tissue is clamped, of a location of the clamped tissue 90, e.g., a location between proximal and distal ends of the surgical stapler 410. In particular, the location condition may be indicative of the location of the pressure points detected by the plurality of sensors 420 caused by the clamping of the tissue 90 by the surgical stapler 410.

In some surgical procedures, it may be desirable to have feedback as to where the tissue 90 is located between the first jaw 418 and second jaw 416 to ensure proper cutting and stapling of the tissue in one single actuation. In other words, the user (surgeon or robotic system) may wish to target a specific location of a tissue to transect. Thus, some means of feedback may be desirable so that the user will know that the surgical stapler 410 has been properly positioned within the surgical site for the first jaw 418 and second jaw 416 to appropriately clamp the tissue 90 at the target site. Thus, the tissue 90 may be clamped a number of times (each time the user receives parameter feedback via the measurements from the sensor array 404 of the tissue sensor 400) until the user is satisfied with the parameters received.

In some instances, when sealing a blood vessel or the like, for example, the user may want to know that the vessel, and only the vessel, is within the jaws in the proper location in the jaws, so as to properly cut and seal. Therefore, the tissue sensor 400 provides an indication to the user to identify when there is pressure in the middle of the jaws but not at the proximal or distal ends of the jaws.

In response to the tissue 90 being clamped over time (i.e., either in the same clamping actuation or across multiple clamping actuations), the controller 481 may adjust the measurement of the parameters. The adjusted measurements may dynamically vary based on the clamping of the tissue 90. For example, the sensed force or pressure of the tissue 90 may decrease as fluid is forced out of the tissue 90 due to the clamping. As discussed above, there may be a period of time required before the readings and measurements stabilize (i.e., stop fluctuating or changing). The controller 481 and/or user may take this waiting time into consideration once the tissue 90 is clamped. In some embodiments, the current value of the adjusted measurements may be indicative of tissue characteristics, clamping positioning, or tissue characteristics and clamping positioning at the time of the measurement.

In some embodiments, the user may dynamically adjust operation of the surgical stapler 410 based on the adjusted measurements. In some embodiments, for example, when the user is a robotic system, the processor 482 of the computer device 470 may cause automatic adjustment of the operation of the surgical stapler 410 as a function of the adjusted measurement. The automatic adjustment may have benefits for certain tissue conditions. Examples of the automatic adjustment of the operation of the surgical stapler 410 may include moving the location of the jaws, increasing, or decreasing the force applied to the jaws, adjusting the transection (e.g., firing) length, and the like. Other examples of the automatic adjustment may include adjusting the speed of the functions of the surgical stapler 410, such as adjusting transection speed during firing (either dynamically along the length or a different constant value for the entire length).

In some embodiments, the processor 482 may be configured to cause at least the adjusted measurement to be displayed on the display.

In some embodiments, the transmission system 406 communicates with the sensor array 404 and may wirelessly transmit, via a wireless network, signals indicative of different data measured by the sensor array 404 to different devices such as processors of computers located outside of the body. In some embodiments, the computer may comprise a display coupled with the processor 482. The display may show different characteristics of the tissue 90 and the surgical stapler 410 based on the received signals.

FIG. 17 illustrates an alternative tissue sensor 500 disposed between a first jaw 518 and a second jaw 516 of a surgical stapler or surgical stapling instrument 510 and a tissue 90. The tissue sensor 500 is configured to be used with the surgical stapler 510 and the tissue 90. It will be appreciated that the surgical stapler 510, the first jaw 518, the second jaw 516, the controller 581, and the transmission system 506 may be used in place of the end surgical stapler 410, the first jaw 418, the second jaw 416, the controller 481, and the transmission system 406 respectively shown in FIG. 16.

Similar to the tissue sensor 400 discussed above, the tissue sensor 500 includes a flexible substrate 502, a sensor array 504, a controller 581, and a transmission system 506.

In some embodiments, the flexible substrate 502 is configured to be disposed on opposite surfaces of the tissue 90, such that the tissue 90 is disposed between the flexible substrate 502. In other words, the tissue 90 is at least partially sandwiched between the flexible substrate 502 that is at least partially wrapped around the tissue 90. Similar to above, the flexible substrate 502 is disposed between the tissue 90 and the surgical stapler 510.

The sensor array 504 may comprise proximity sensors, e.g., magnetic, optical, Hall effect and the like, disposed on different regions of the flexible substrate 502 such that the proximity sensors may be disposed on opposite surfaces of the tissue 90. For example, one side may include the proximity sensors and the other side may include something detected by the proximity sensors. For example, if a Hall effect sensor is on one side, a magnet (or electro magnet) may be disposed on the other side or opposite surface of the tissue 90. In some instances, if one side of the flexible substrate 502 has an impedance sensor, the other side may have an electrical emitter, and the like. In other examples, both sides of the flexible substrate 502 may include metal plates which form a capacitor with the tissue 90 disposed in between the flexible substrate 502 and the tissue sensor 400 may measure a capacitance. In other instances, one side may have optical detectors and the other side may have LED's and the like. In other words, as the tissue sensor 500 is clamped, the sensor array 504 is configured to sense different parameters indicative of characteristics of the first 518 and second jaws 516, and different characteristics of the tissue 90. The parameters may be indicative of a clamping condition, a distance condition of the first jaw 518 or the second jaw 516, a location condition of the first jaw 518 or the second jaw 516, or combinations thereof. The location condition further explained below may be indicative of the location of the pressure points detected by the plurality of sensors 520 exerted by the first 518 and second jaw 516 when clamping the tissue 90.

The distance condition may be indicative of a distance or a gap between a distal end of the first jaw 518 and a distal end of the second jaw 516. The distance or gap may be indicative of thickness or compressibility of the clamped tissue 90.

In particular, the controller 581 may be configured to, based on the processed signals, determine a measurement of a distance between a distal end of the first jaw 518 and a distal end of the second jaw 516 when the tissue 90 is clamped. The controller 581 may be further configured to, based on the measurement of the distance, determine a thickness or compressibility of the clamped tissue 90. The controller 581 may be configured to, when the tissue 90 is clamped, based on the processed signals, determine a location of proximal and distal ends of the first jaw 518 or between proximal and distal ends of the second jaw 516 in the tissue sensor 500.

As mentioned above, in some embodiments, the proximity sensors may include Hall effect sensors and magnets. As the tissue sensor 500 is clamped, the Hall effect sensors may be configured to detect changes in a magnetic field surrounding the Hall effect sensors caused by the movement of the tissue sensor 500 being clamped by the first jaw 518 and the second jaw 516 of the surgical stapler 510 (due to changes between the Hall effect sensors and a corresponding magnet). In particular, when compression of the tissue 90 and the tissue sensor 500 occurs, the gap between the first jaw 518 and the second jaw 516 changes. Since the Hall effect sensors are disposed in the flexible substrate 402 on one side of the tissue 90 and magnets are disposed in the flexible substrate 502 on the other side of the tissue such that the flexible substrate 502 is disposed on opposite sides of the tissue 90 (due to the flexible substrate 502 being wrapped around the tissue 90), the Hall effect sensors are able to detect a distance between the jaws which is indicative of the thickness or compressibility of the clamped tissue 90. In some embodiments, when computing the thickness of the tissue 90, the thickness of the substrate 502 containing the sensor array 504 may be considered. For example, if the proximity sensors are located on an outer surface of the substrate 502, the distance detected between the proximity sensors on opposite sides of the tissue 90 would include the thickness of the substrate 502 on both sides of the tissue 90. Removing the thickness of the substrate 502 from the calculation, the distance between the two proximity sensors without the substrate 502 leaves just the thickness of the tissue 90.

In some embodiments, the sensor array 504 may include proximity sensors, force sensors, location sensors, or combinations thereof disposed in an array. In particular, the sensor array 504 may further include force sensors which, as mentioned above, sense and detect the pressure in response to the force 454 exerted by the surgical stapler 410 on the clamped tissue 90 and the tissue sensor 500, or, in other words, sense and detect pressure in response to a force applied to actuate the surgical stapler 410 to clamp the tissue 90 and the tissue sensor 500 together. Therefore, the tissue sensor 500 may be configured to measure both force and thickness characteristics of the clamped tissue 90. A force sensor may include a piezoelectric sensor, resistive/capacitive foam sensors, or any type of force sensor, now known or later developed. The sensors of the sensor array 504 may further act as location sensors which, as mentioned above, detect a parameter indicative of the location of the pressure exerted by the surgical stapler 510 including the first jaw 518 and the second jaw 516. In other words, sensors of the sensor array 504 that detect pressure (or the highest amount of pressure) indicate where along the sensor array 504 the jaws are being clamped. Therefore, the tissue sensor 500 may be configured to measure force, location of the force, thickness of the tissue 90, or combinations thereof. In particular the controller 581 of the tissue sensor 500 may derive, detect, or measure force, location of the force, thickness of the tissue 90, or combinations thereof based on the received signals from the plurality of sensors 420.

Figure 18:
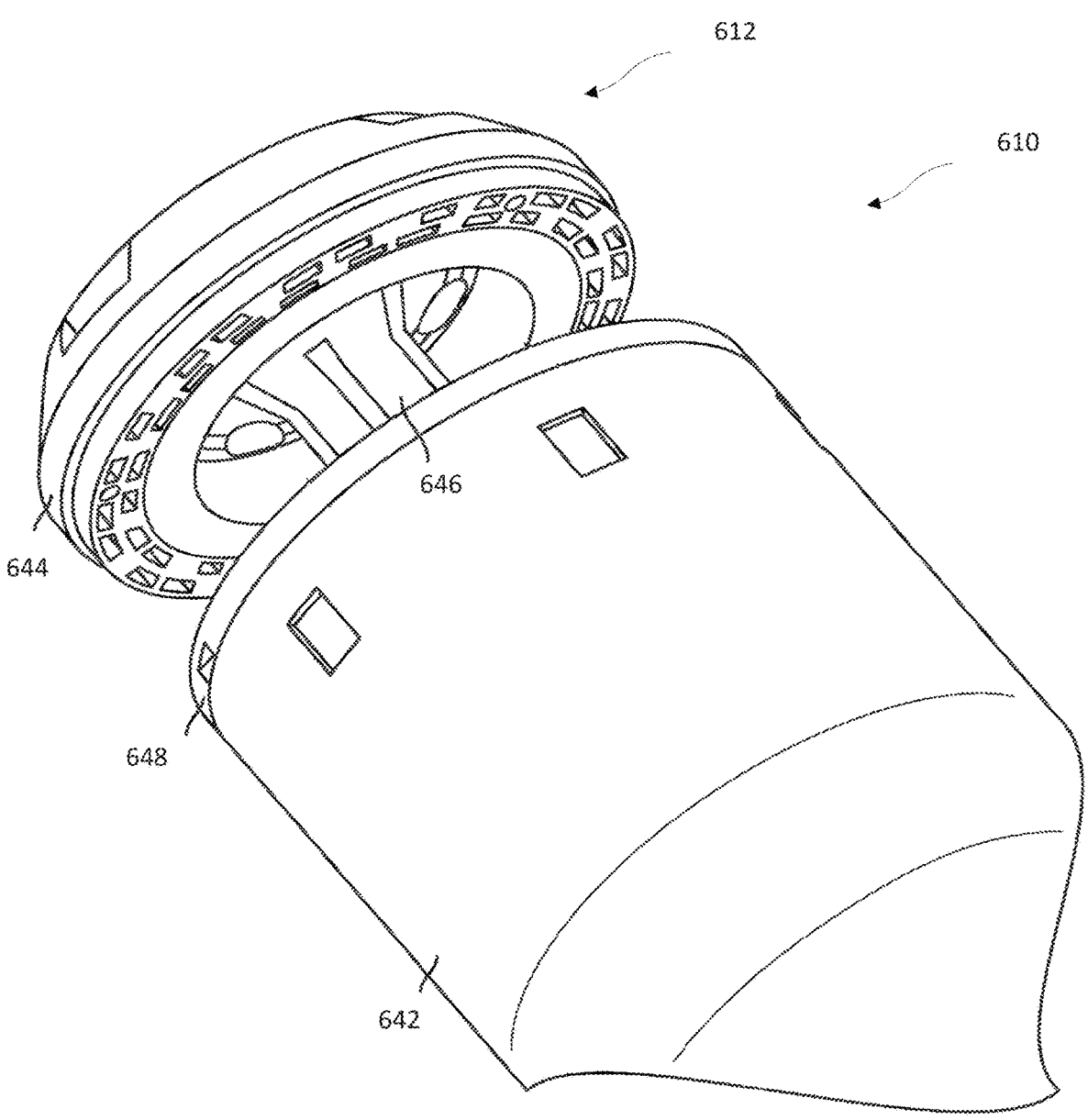
FIG. 18 illustrates one embodiment of a head of a circular stapler.

Although the various embodiments so far described comprise first and second jaw members pivotally coupled, the described embodiments are not so limited. For example, in one embodiment, a surgical stapler 610 may include an end effector which may comprise a circular stapler end effector 612 as shown in FIG. 18. The circular stapler end effector 612 comprises a body 642. The body 642 may be coupled to a shaft 646, such as, for example, the shaft assembly 200 of the surgical instrument 10. The body 642 is configured to receive a staple cartridge and/or one or more staples therein (not shown). An anvil 644 is moveably coupled to the body 642. The anvil 644 may be coupled to the body 642 by, for example, the shaft 646. The shaft 646 is receivable within a cavity within the body (not shown). In some embodiments, a breakaway washer 648 is coupled to the anvil 644. The breakaway washer 648 may comprise a buttress or reinforcing material during stapling.

Figure 19:
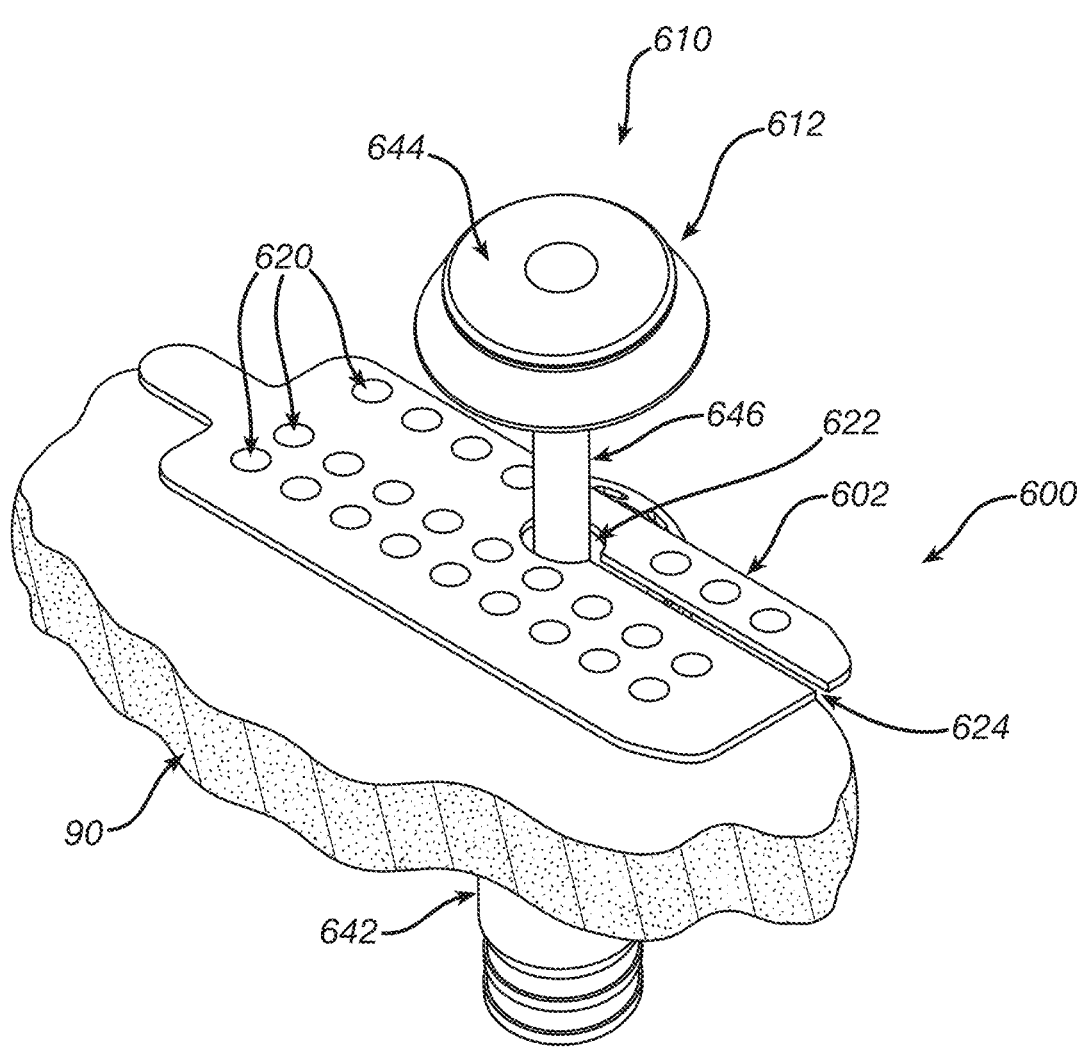
FIG. 19 depicts an alternative tissue sensor according to one embodiment.

FIG. 19 illustrates an alternative tissue sensor 600 disposed between the circular stapler end effector 612, shown in FIG. 18, and a tissue 90. The tissue sensor 600 is configured to be used with the circular stapler end effector 612 and the tissue 90.

The tissue sensor 600 includes a flexible substrate 602 configured to be disposed between the anvil 644 and the body 642 of the circular stapler end effector 612. The flexible substrate 602 includes an opening 622 with a slit 624 through one side to enable ease of installation and removal via the shaft 646. To use the tissue sensor 600 of FIG. 19, a user would align the slit 624 of the flexible substrate 602 with the shaft 646 of the circular stapler end effector 612 and slide the tissue sensor 600 into position, either between the anvil 644 and the tissue 90 or the body 642 and the tissue 90, until the shaft 646 is positioned in the opening 622 of the flexible substrate 602. As the circular stapler end effector 612 is actuated, the anvil 644 and body 642 are forced toward each other, compressing the tissue 90 and tissue sensor 600 therebetween.

In some embodiments, the tissue sensor 600 comprises a plurality of sensors 620. The plurality of sensors 620 is configured to detect one or more parameters of the circular stapler end effector 612 and/or a tissue section 90 located between the body 642 and the anvil 644. In one embodiment, the tissue sensor 600 may be disposed between the tissue 90 and the anvil 644. In another embodiment, the tissue sensor 600 may be disposed between the tissue 90 and the body 642. In some embodiments, the tissue sensor may be disposed on opposite surfaces of the tissue 90 between the anvil 644 and the body 642. The plurality of sensors 620 may be arranged in any suitable arrangement, such as, for example, being equally spaced about the perimeter of the substrate 602. The plurality of sensors 620 may comprise any suitable sensors for detecting one or more parameters of the circular stapler end effector 612 and/or a tissue section 90 located between the body 642 and the anvil 644. For example, the plurality of sensors 620 may comprise magnetic sensors, such as a Hall effect sensor, strain gauges, pressure sensors, inductive sensors, such as an eddy current sensor, resistive sensors, capacitive sensors, optical sensors, any combination thereof, and/or any other suitable sensor.

In some embodiments, each of the plurality of sensors 620 is configured to detect a pressure generated by the presence of compressed tissue between the body 642 and the anvil 644. In some embodiments the plurality of sensors 620 are configured to detect the impedance of a tissue section 90 located between the anvil 644 and the body 642. The detected impedance may be indicative of the thickness and/or fullness of tissue 90 located between the anvil 644 and the body 642. The plurality of sensors 620 generate a plurality of signals indicative of the detected pressure. The plurality of generated signals is provided to a controller, such as the controller 481, or to a processor, such as, for example, the processor 482 discussed above. The controller 481 or the processor 482 applies one or more algorithms and/or look-up tables based on the input from the plurality of sensors 620 to determine one or more parameters of the circular stapler end effector 612 and/or a tissue section 90 located between the body 642 and the anvil 644. For example, in one embodiment comprising a plurality of pressure sensors, the controller 481 or the processor 482 is configured to apply an algorithm to quantitatively compare the output of the plurality of sensors 620 with respect to each other and with respect to a predetermined threshold. In one embodiment, if the delta, or difference, between the outputs of the plurality of sensors 620 is greater than a predetermined threshold, feedback is provided to the user indicating a potential uneven loading condition.

Figure 21:
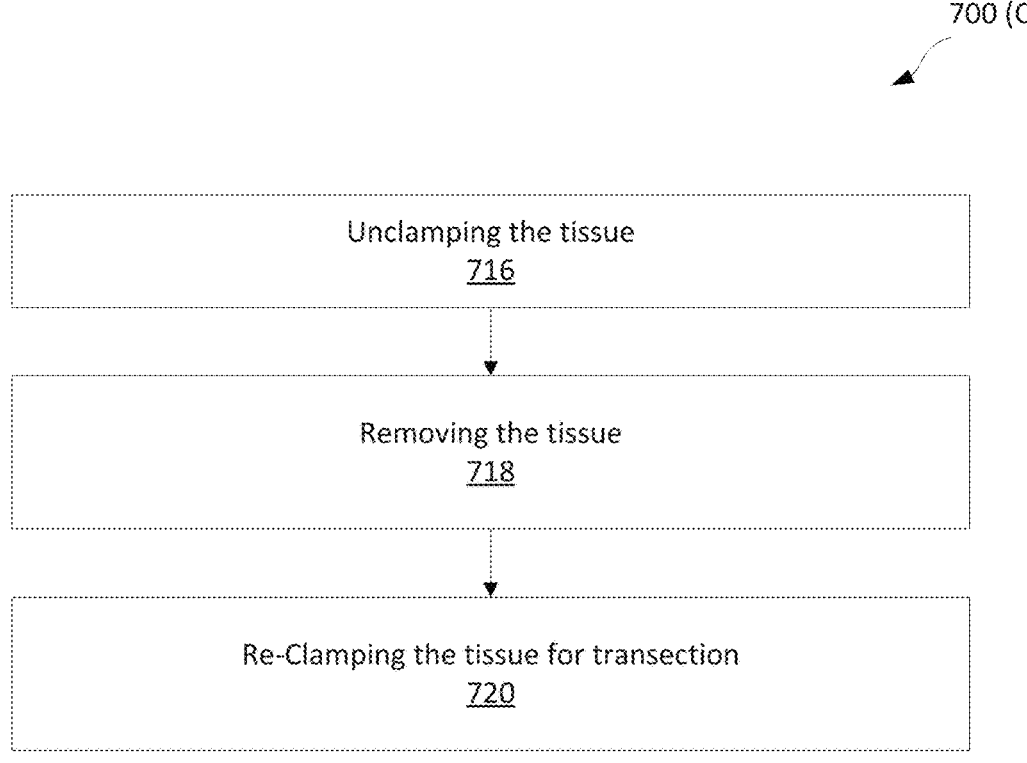

FIGS. 20 and 21 depict flow chart depicting an operation or a process 700 for the operation of the tissue sensor 400 and 500 and the surgical stapler 410 and 510 shown in FIGS. 16 and 17 for measuring characteristics of the tissue 90.

The process 700 may include targeting, by a user of the surgical stapler 410, a tissue 90 for transection (Block 702). The process 700 may further include disposing the tissue sensor 400 on the tissue 90 (Block 704). In one embodiment, the tissue sensor 400 may be disposed between the tissue 90 and jaws of the surgical stapler 410 (or between the tissue 90 and the anvil 644 and the body 642 of the circular stapler 612 of FIGS. 18 and 19). The process 700 may further include clamping, by the jaws of the surgical stapler 410 (or by the anvil 644 and the body 642 of the circular stapler 612 of FIGS. 18 and 19), the tissue 90 and the tissue sensor 400 (Block 706). The process 700 may further include sensing, by the tissue sensor 400 disposed on the tissue 90, a mechanical force as input in response to the clamping of the tissue 90 and the tissue sensor 400 by the surgical stapler 410 (Block 708). The process 700 may further include converting, by the tissue sensor 400, the sensed force into an electrical output signal that can be measured (Block 710). As the force applied increases, the electrical signal changes proportionally. The converted electrical output signal may be indicative of the thickness and/or fullness of the tissue 90 clamped by the surgical stapler 410. The process 700 may further include transmitting, by the tissue sensor 400 to the processor 482, a plurality of signals 440 including the converted electrical output signal (Block 712). The process 700 may further include controlling, by the processor 482, the surgical stapler 410 based on the plurality of signals 440 (i.e., based on the electrical output signal(s)) (Block 714).

In some embodiments, the process 700 may further comprise, partially unclamping the surgical stapler 410 from the tissue sensor 400 and the tissue 90 to allow the tissue sensor 400 to be removed (Block 716). In other words, the surgical stapler 410 may be unclamped from the tissue sensor 400 and the tissue 90 enough to allow the tissue sensor to be removed while keeping the tissue in place instead of fully unclamping. This avoids the tissue from moving and receiving measurements that are not accurate due to the movement. The process 700 may further include re-clamping, by the surgical stapler 410, the tissue for transection (Block 720). In some embodiments, the unclamping, removing, and re-clamping as shown in Blocks 716-720 may be performed by the first 418 and second jaws 416 of the surgical stapler 410 or the anvil 644 and the body 642 of the circular stapler 612 of FIGS. 18 and 19.

To remove the tissue sensor 400, the surgical stapler 410, including the jaws of the surgical stapler 410, may be used to grasp and roll up the tissue sensor 400 to be removed through the trocar. In another example, the tissue sensor 400 may include a pull point, such that the tissue sensor 400 collapses on itself as it is pulled out of the body. In yet other examples, such as during open surgery, the tissue sensor 400 may easily be removed. The disclosed system and methods may also include an alert that alerts a user if/when the tissue sensor 400 is left in the body.

V. Pressure Sensitive Film for Measuring Tissue Compression Along Length of Jaw

Currently, mechanically pressure sensitive films may be used for medical use cases such as to measure feet sore pressure, orthopedics, bone plate pressure, tooth alignment and pressure, laminating processes, gasket sealings, and other pressure monitoring systems due to the ease of monitoring pressure by color visualization (i.e., color mapping) without the need for additional electronic wiring.

In some embodiments, in particular for open surgical devices as shown in FIG. 22 as opposed to endoscopic devices discussed above, a pressure sensitive film may be used as an alternative tissue sensor to sense and measure the compression force applied by the jaws of a surgical instrument during operation and provide feedback to the user. The pressure sensitive film may be disposed either on a first jaw or a second jaw, the channel of the second jaw, or other areas of the open surgical instrument (e.g., the handle, etc.) to infer the pressure applied by the first and second jaws qualitatively. The placement of the pressure sensitive film enables sensing and measuring of the distance between the jaws and the compression force applied by the first and second jaws during operation to provide feedback to the user.

The pressure ranges of the pressure sensitive film may range from 0.05 MPa to 300 MPa. The precision may be +/−10%. Due to possible sensitivity, the film may be sterilized using hydrogen peroxide. The temperature of the operating room may be set to 68F-95F. The humidity may be set to 35%-80%.

In particular, the pressure sensitive film may be disposed between the jaws and the tissue to measure the pressure. Once pressure is applied, to determine the approximate pressure value, the resulting coloring distribution displayed in the film may be compared with a color chart. A calibration curve may also be used to verify the approximate pressure value.

As shown in FIG. 22, the pressure sensitive film 800 may be a two-sheet type Prescale available from Fujifilm. The two-sheet type sheet may be composed of two films which are respectively coated with color-forming material and color-developing material. The two type sheet may be used by placing the sides coated with the chemical agents over each other. One film may include a polyester base and a micro-encapsulated color-forming layer. The other film may include a polyester base and a color-forming layer. The microcapsules in the color-forming layer are broken by pressure, and the colorless dye is absorbed into the developer, causing a chemical reaction to produce a color, such as red. The microcapsules containing the color-forming material are adjusted to varying sizes and strengths, and are coated uniformly, producing a color density that corresponds to the amount of pressure.

FIG. 22 further depicts an example of the pressure sensitive film disposed in open surgical staplers 802 and 804. The film displays different color shades based on the pressure applied by the open surgical stapler. The even color shown in the pressure film 800*a* disposed in the open surgical stapler 802 is indicative that pressure is evenly applied. The uneven color shown in the pressure film 800*b* disposed in the open surgical stapler 804 is indicative that pressure is not evenly applied. As can be seen, the visual check and the assessment may be performed by a user or may be incorporated with trained advanced imaging to determine a "PASS" or a "FAIL" assessment. In other words, when pressure is applied evenly, the visual indication of the even color pattern indicates a "PASS" meaning that the tissue is properly positioned and clamped, whereas when pressure is applied unevenly, the visual indication of the uneven color pattern indicates a "FAIL" meaning that the tissue is not properly position and clamped. The incorporation of the pressure sensitive film in the jaws or a buttress style attachment may be used as a training tool to assess tissue viability.

VI. Pressure Sensitive Film on Reload for Stapler Pressure Monitoring

Figure 23:
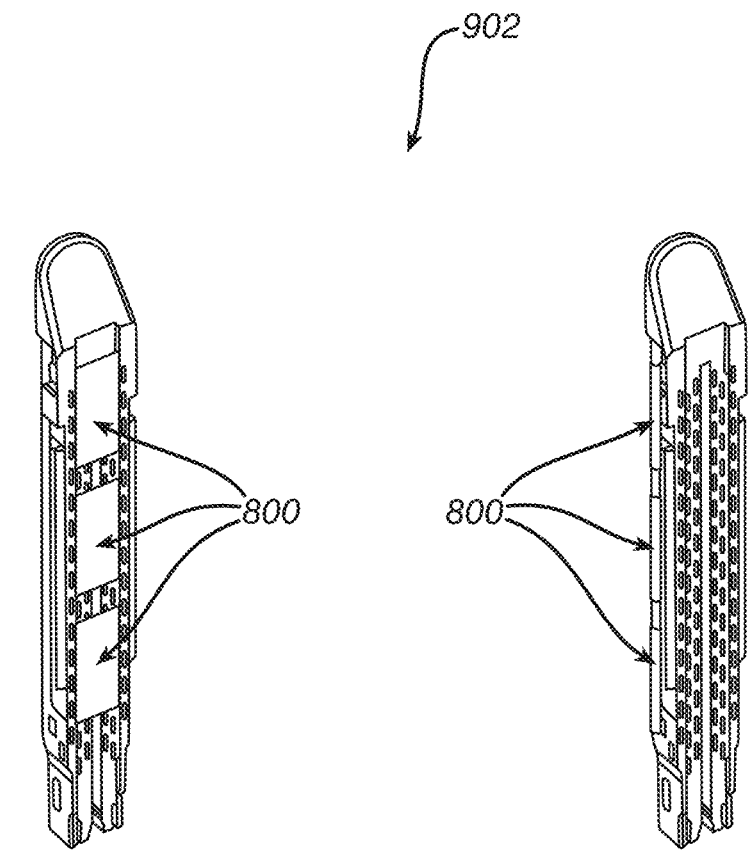
FIGS. 23A and 23B depict an example of a pressure sensitive film disposed on a cartridge according to one embodiment.

As mentioned above, in certain circumstances it may be difficult for a user (surgeon or robotic system) to figure out or determine tissue compressibility and a tissue compressed thickness at a target site. In turn, this makes it difficult for the user to determine what staple cartridge to select, or whether the cartridge already selected is proper for the targeted tissue. Therefore, in some embodiments, as shown in FIGS. 23A and 23B, a sacrificial reload or "dummy" cartridge including pressure sensitive film(s) 800 (such as those discussed above) may be used, where the pressure sensitive film may be disposed on either the top of the stapler reload as shown in FIG. 23A or on the bottom of the stapler reload as shown in FIG. 23B to map out the pressure for the stapler process. The pressure sensitive film may include a number of discreet film segments, such as those shown in FIGS. 23A and 23B, or one continuous piece of film that spans the length of the cartridge.

The user may place the dummy cartridge containing the pressure sensitive film into the cartridge channel of one of the jaws of the surgical stapler, place the surgical stapler at the target site, and clamp the jaws on the tissue at the target site. As discussed above, when pressure is applied and the jaws clamp down on the tissue, the color of the pressure sensitive film may be indicative of the compression force applied by the jaws, which provides direct feedback to the user regarding the pressure mapping for the stapler process. The color of the pressure sensor film can be quantified via a processor or in most cases even with visual recognition of the color difference. Once the correct pressure mapping is known, the user may discard the sacrificial cartridge and replace it with the proper cartridge for the target tissue. As noted above, an advantage of using pressure sensitive film in this way is that a user can determine the pressure map by color visualization and no electronic wires or other connection is needed. This provides a quick and easy way to figure out pressure mapping for a stapling procedure.

VII. Visual Clamping Force Sensing for Endocutter or Open Stapler

As mentioned previously, in some instances, it may be very difficult for the user, e.g., a surgeon or a robotic system, to figure out the compressibility and compressed thickness of a tissue when the jaws of an instrument, e.g., an endocutter or an open surgical stapler, are clamped on the tissue. It may be uncertain whether a previously selected staple cartridge is appropriate for the targeted tissue. If the selected type and height of the staple do not match the compressed thickness of the targeted tissue, the sealing outcome may not be optimal. In particular, the tissue thickness and density in the jaws may be a critical input for selecting a staple cartridge to provide the optimal compression to achieve optimal surgical results.

Figure 24:
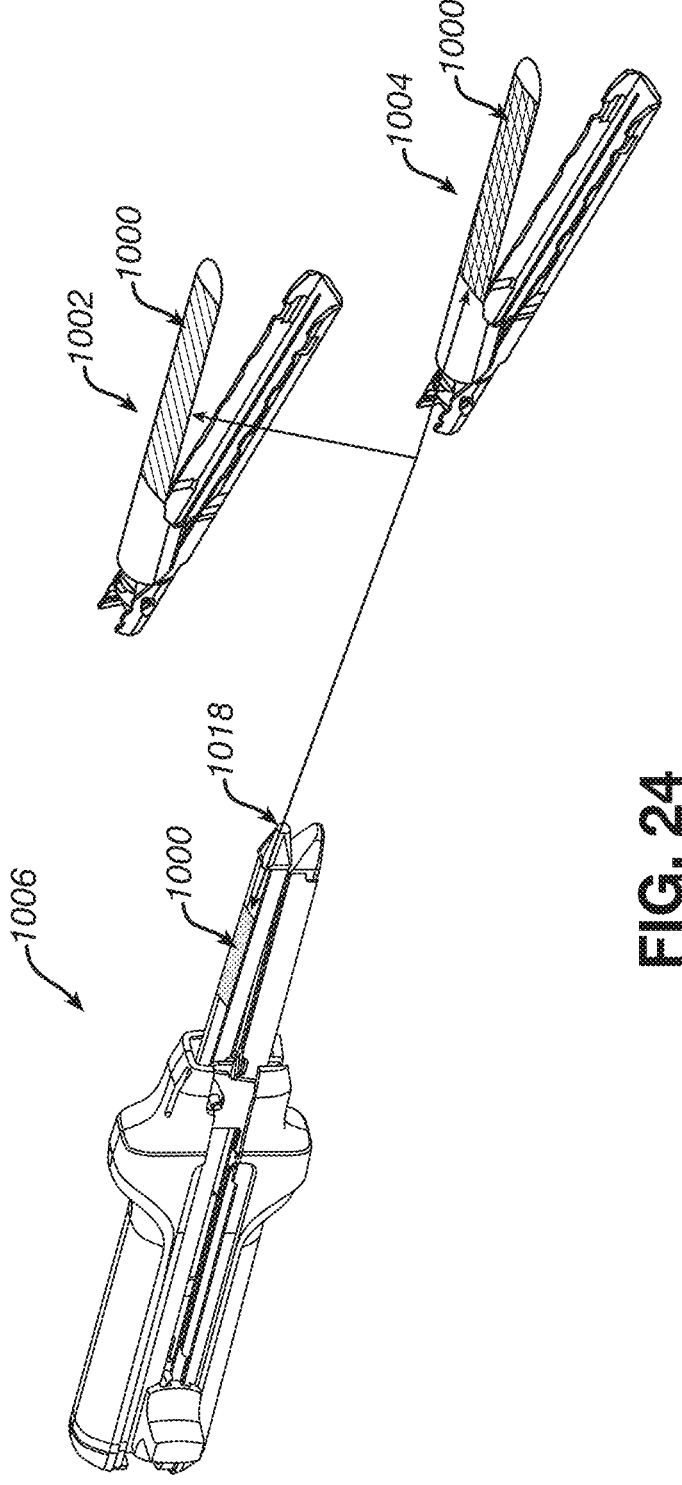
FIG. 24 depicts an alternative tissue sensor according to one embodiment.

In some embodiments, as shown in FIG. 24, in response to a clamping of a tissue, an alternative tissue sensor 1000 may include a self-powered visualized flexible pressure sensor (SP-VFPS) that may be used to provide a visual indication of deflection of an anvil jaw 1018 of a surgical stapler instrument 1006, such as the anvil jaw 1018 of the open surgical stapler 1006 shown in FIG. 24. The SP-VFPS may be attached or applied to the anvil jaw 1018. In some embodiments the visualized flexible pressure sensor may be configured as a separate device which is disposed by the user prior to using the instrument or in other embodiments it may be integrated as part of the manufacturing of the stapler device.

In some embodiments, the SP-VFPS may include color-tunable triboelectrification-induced electroluminescence (TIEL). As the anvil jaw 1018 deflects due to tissue pressure, the SP-VFPS may change colors. The visual signal may include different colors relative to a tissue thickness threshold value. For example, a green color in the alternative tissue sensor 1000 of the stapler device 1002 may alert the surgeon that the tissue thickness is appropriate for the staple cartridge selected. A red color in the alternative tissue sensor 1000 of the stapler device 1004 may be indicative that the tissue thickness is too wide or thick relative to the thickness threshold value. An unchanged color in the alternative tissue sensor 1000 of the stapler device 1006 may be indicative that the tissue is too thin relative to the thickness threshold value.

In some embodiments, when the color displayed is "green," the color green provides a visual indication including information feedback indicative that the compressive force applied to the tissue is within a desired range. If the indication is "red," the red indication may cause the surgeon or may control the robotic system to take a first action. The first action may include unclamping the jaws and changing the staple cartridge to a taller staple cartridge. If the indication is "neutral," i.e., no change in color, the neutral indication may cause the surgeon or may control the robotic system to take a second action. The second action may include unclamping and selecting a shorter staple cartridge.

Therefore, the different colors displayed may provide a visual indication indicative of tissue compression information that provides the surgeon or robotic system with feedback on whether the selected staple cartridge is appropriate for the targeted tissue prior to the firing.

VIII. Smart Cartridge for Measuring Pressure Pattern and Tissue Gap

Figure 25:
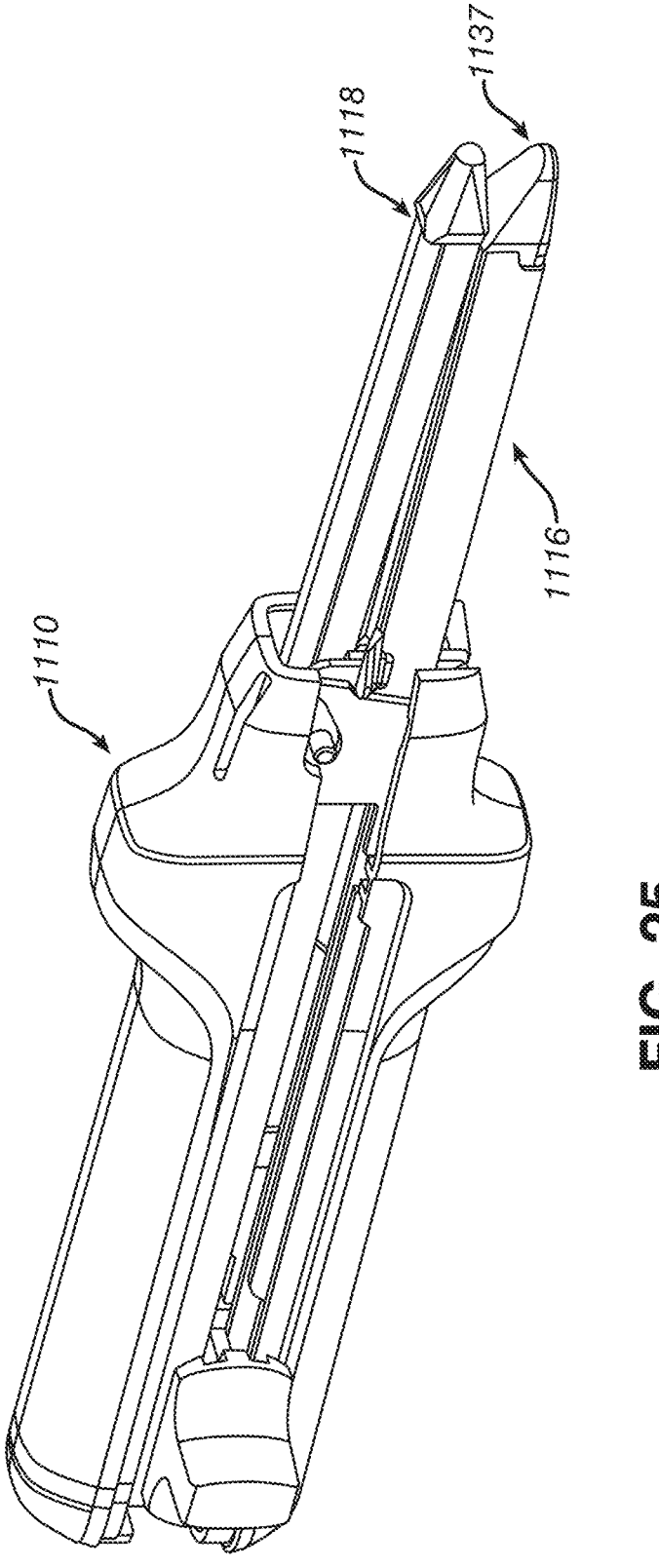
FIGS. 25-28 depict an alternative tissue sensor according to one embodiment.
Figure 26:
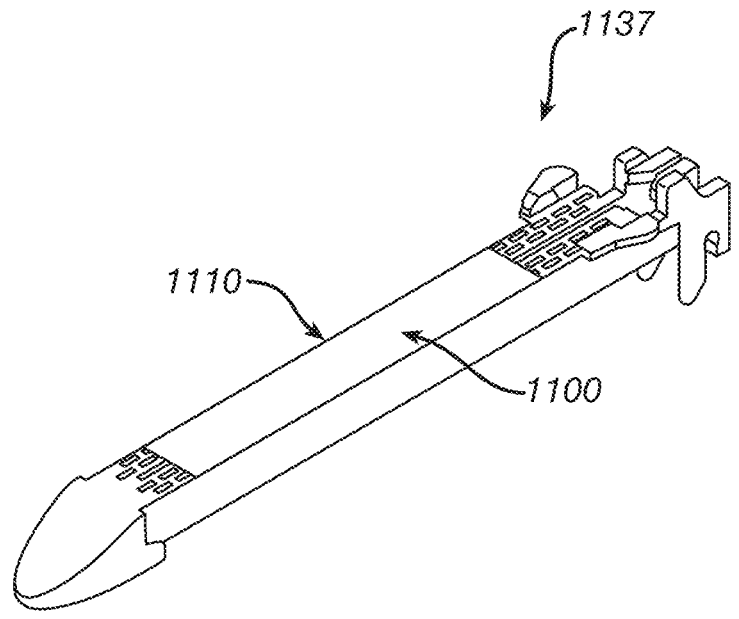
Figure 27:
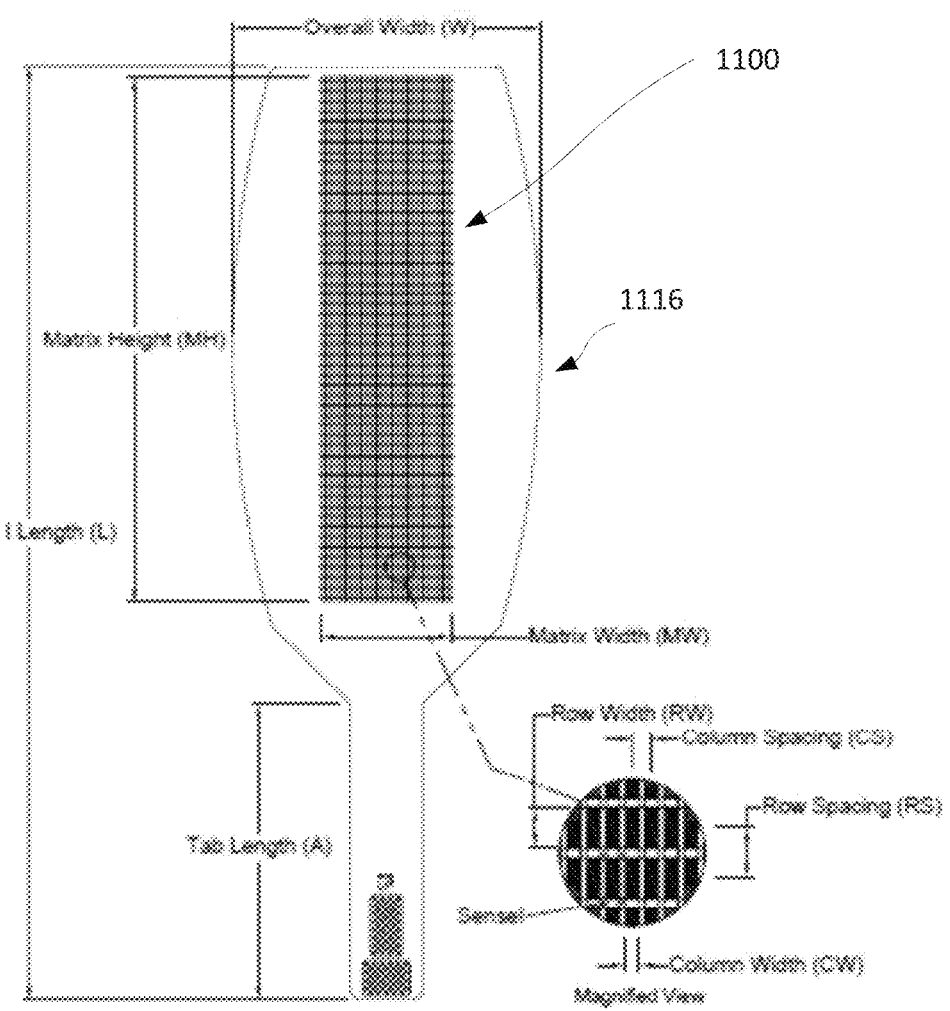

In some embodiments, as shown in FIGS. 25-27, a lower jaw 1116 of an instrument 1110 may include a channel to accept a smart cartridge 1137 that may be used for detection of the pressure patterns across the face of the staple cartridge and tissue gap. It will be appreciated that the upper jaw 1118 and the lower jaw 1116 may be used in place of the first jaw 418 and the second jaw 416 respectively shown in FIG. 16.

Instead of including staples, the smart cartridge 1137 may include an energy cell and a transmitter to send information via Bluetooth to a device to interpret data and provide a real time sensor display to the user. An alternative pressure sensor 1100 including a pressure sensitive film may be loaded in the smart cartridge 1137 to provide a pressure distribution pattern. The pressure sensitive film may detect the pressure across the cartridge face creating a pattern for review. The smart cartridge 1137 may measure the distance between the jaws (tissue gap) which is indicative of tissue thickness by means of a magnet and sensor embedded in the smart cartridge 1137. The pressure sensitive film may be a pre-scale pressure film provided by Fujifilm or a thin film sensing grid provided by Tekscan. The detected pressure and the tissue thickness may be indicative of tissue health, at what speed the surgical stapler 410 may perform different functions and may be used to determine a consistent measurement of tissue thickness. For example, a tissue thickness may be measured at a consistent pressure (e.g., 5 lbs./inch) on average across the cartridge as opposed to measuring the tissue thickness at any pressure. In other words, the tissue thickness measured would be a function of pressure applied, and the pressure sensitive film may be used to monitor and maintain a constant pressure while taking thickness measurements. In another example, the pressure may be used for determining the type/health of the tissue 90, for example, using different stiffness curves.

In particular, the smart cartridge 1137 may provide information to the user on the tissue thickness and clamping compression pattern. Data feedback from a receiving device may determine the best cartridge (for the appropriate staple height) for the tissue based upon the device position, compression, and tissue gap feedback. The data collected may be used for future correlation of formed staple height.

Figure 28:
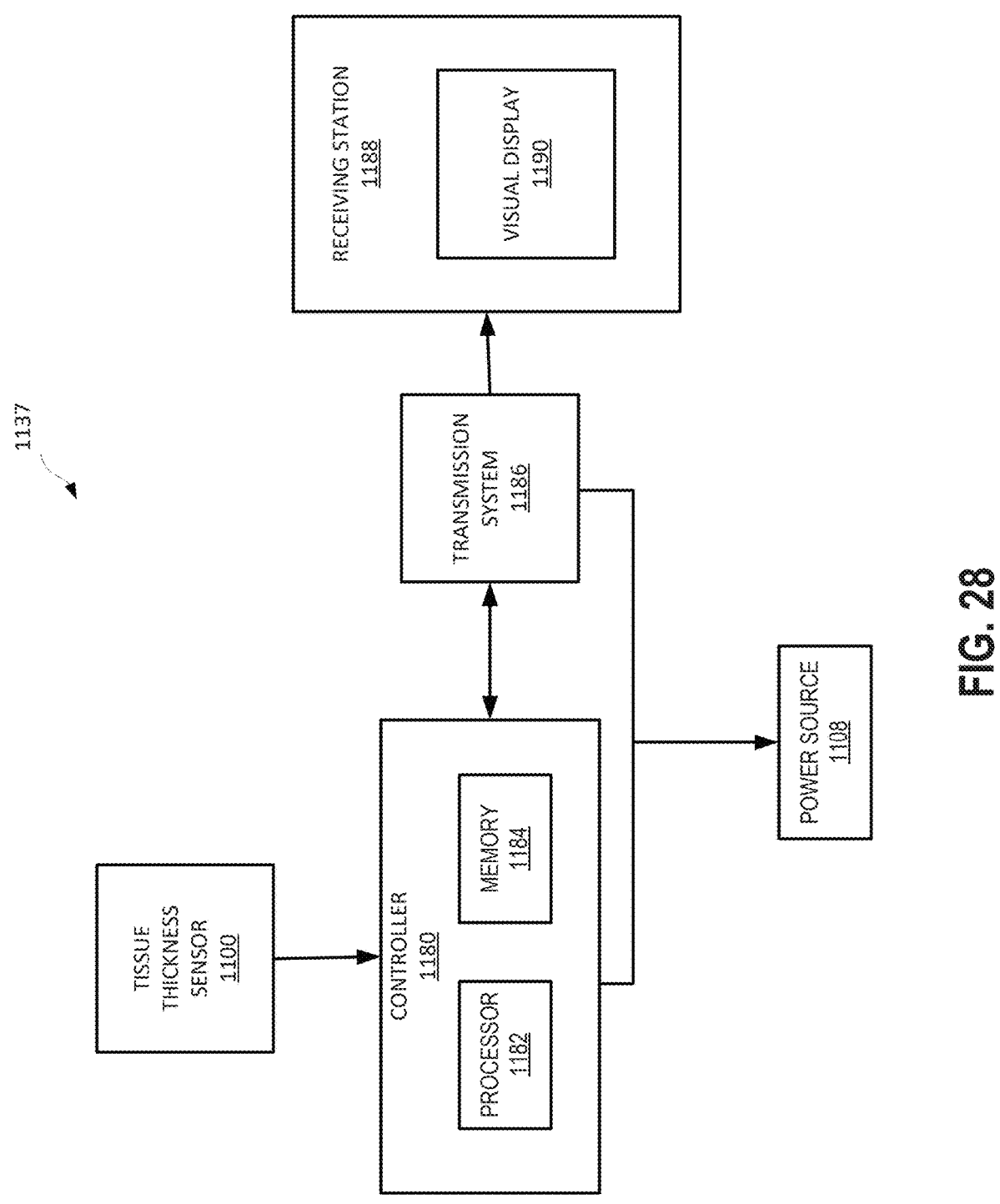

As shown in FIG. 28, the smart cartridge 1137 may include a power source 1108 to provide power, a controller 1180, a processor 1182, a memory 1184, and a transmitter or transmission system 1186 including a radio module for signal communication. The memory 1184 contains computer executable instructions executed by the controller 1180 to cause the controller to receive data from the tissue thickness or pressure sensor 1100. The memory 1184 may further include computer-executable instructions that when executed by the controller 1180, cause the controller 1180 to interpret, process, and provide data containing measuring information via the radio module 1186 to a receiving station 1188 for interpretation and to display and present the pattern for the user via a visual display 1190. The receiving station 1188 may include a computer device. The memory 1184 stores historical data of previous measuring information for correlation of tissue condition and formed staple height. The controller 1180 retrieves the data from the memory 1184 and provides the user with historical data and real time feedback on the tissue thickness and the clamping pressure across the tissue via the visual display 1190. The controller 1180 further provides feedback data on the tissue condition based upon historical data stored in the memory 1184. The data provided enables more precise cartridge selection. For example, the controller 1180 may provide the expected force required to fire the instrument 1110 via the visual display 1190, which may be particularly beneficial for manual devices. The controller 1180 may further provide and display, via the visual display 1190, pressure data such as pressure distribution data, real-time pressure sensor data in 2D and 3D, peak pressure, and center of force.

IX. Dedicated Open Instrument for Measuring and Designating Tissue Targets

In some instances, once the property of the tissue is measured and evaluated, it may be difficult to know the exact location where the tissue reading was performed due to the characteristics of the tissue, e.g., as previously mentioned, the tissue may have different variability, biphasic characteristics, or varying thickness. Therefore, there is a need for a dedicated, diagnostic device that accesses, measures, communicates, and marks stapling sites.

In some embodiments, as shown in FIGS. 29A-32, an end effector 1210 may be configured to be used as a dedicated diagnostic device to evaluate tissue targets for open procedures (e.g., low anterior resection (LAR) and bowel resection). The end effector 1210 may be configured to indicate to the user where the measurement of the tissue 90 was taken so that the user may use another stapler instrument and fire on the targeted area. In particular, the end effector 1210 provides access to a clamped tissue 90, manipulates and measures the tissue 90, marks or imprints the tissue 90, and communicates properties of the tissue 90 to, for example, inform reload selection. Therefore, the end effector 1210 measures and marks the tissue 90 so the user is able to find the targeted area without having to take a look at a visual display in a separate computer device (see FIGS. 30 and 31).

Figure 29A:
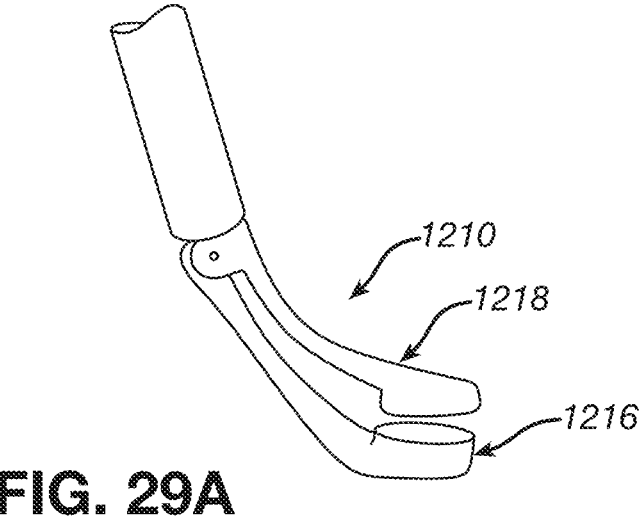
FIGS. 29A and 29B depict a tissue sensor and marker according to one embodiment.
Figure 29B:
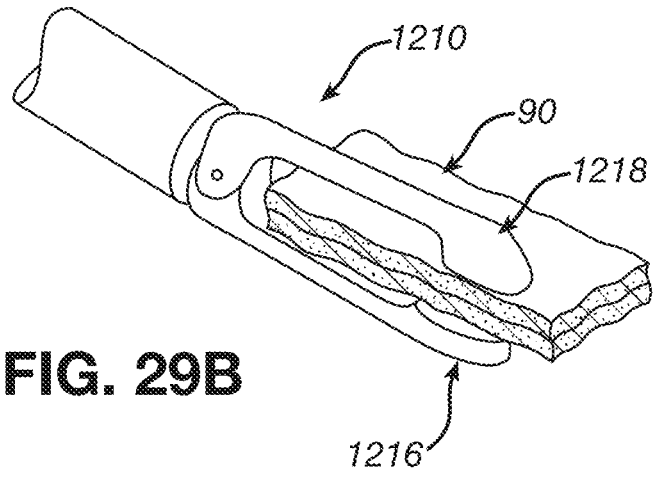

FIGS. 29A and 29B show some embodiments of the end effector 1210 including an upper jaw 1218 and a lower jaw 1216. As shown in FIG. 29B, the end effector 1210 may be configured to access a wide range of open tissues such as the clamped tissue 90 for measurement. In some embodiments, the end effector 1210 may be a curved end effector which includes a curve that is sufficient to enable access to LAR targets but insufficient to make a straight cutter target awkward. The end effector 1210 may include raised pads to isolate regions of the tissue 90.

In some embodiments, the end effector 1210 may perform tissue measurements including thickness measured via a magnet disposed in the upper jaw 1218 and a Hall sensor disposed in the lower jaw 1216, pressure measured via capacitance pads in the upper and lower jaws 1218 and 1216, pressure measured via sensing input clamping force provided by the user, thickness measured via angular encoder in the upper and lower jaws 1218 and 1216, pressure and thickness measured via a light source disposed in the upper jaw 1218, a light sensor disposed in the lower jaw 1216, and embedded electronics to monitor the change in received light as a function of a jaw angle, and pressure measured via perfusion sensors. Other measurement means are possible.

As mentioned above, data indicative of different tissue measurements may be sent via different communication devices including communications, e.g., Bluetooth to USB, to capital equipment in the operating room, e.g., a computer, that may be configured to display data about surgical instruments to a surgeon as well as to provide energy, e.g., a power/energy generator such as monopolar and bipolar energy generators.

Figure 30:
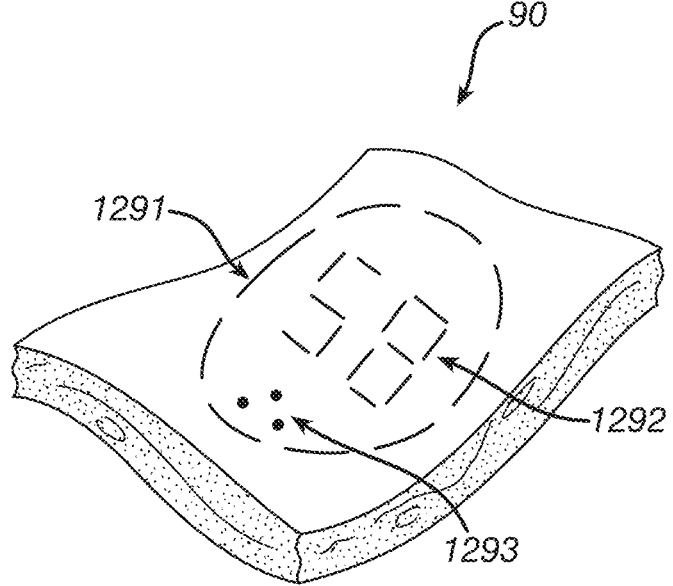
FIGS. 30-32 depict tissue marked using the tissue sensor and marker of FIGS. 29A and 29B.
Figure 31:
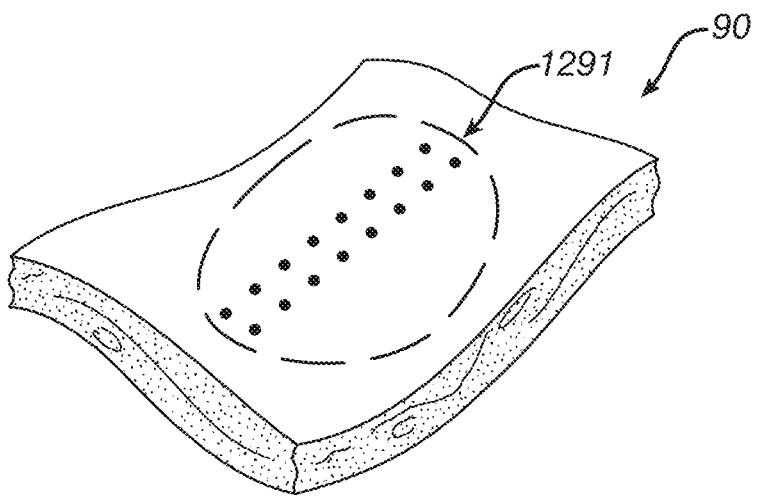

In some embodiments, as shown in FIGS. 30 and 31, the end effector 1210 may be used to mark or imprint tissue within a measurement area 1291. In particular, the ink may be ejected from sites of the end effector 1210. After the user completes a measurement and decides to staple, the user may press a button on the handle of the end effector 1210 that releases ink at the target site. As shown by the dotted lines in FIG. 31, the ink may outline the shape of the end effector 1210. The ink may include properties to glow under UV light for easier location. The ink may outline a number of dots which increment to uniquely label each target side using an indexing dot pattern 1293, (e.g., 1 dot, 2 dots, etc.). The ink may relay a tissue measurement result 1292 (e.g., a measured thickness of the tissue or a specific number associated with a cartridge selection). In some embodiments, if the measurement site is ideal for a blue reload, it could mark "Blue" or use blue ink. In some embodiments, the ink may relay a code, e.g., a QR code, indicative of measured values and tissue characteristics that may be seen using a camera and that may be interpreted by a processing device such as a controller or a processor.

Figure 32:
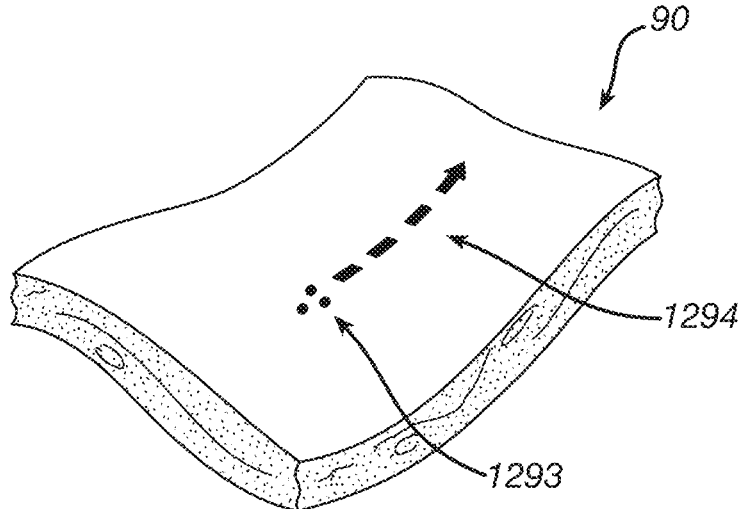

In some embodiments, as shown in FIG. 32, the end effector 1120 may mark the tissue 90 using localized blanching 1294 (e.g., blanched cut line with direction) of the target tissue. In particular, the upper and lower jaws 1218 and 1216 of the end effector 1210 may include bi-polar self-marking energy pads that blanch/scald the target cut lines 1294, the measurement result 1292, and/or the measurement index 1293.

Therefore, the end effector 1210 may be reusable and may combine both communication and marking tissue technology using a common modality.

GENERAL STATEMENTS AND CLARIFICATIONS

In accordance with various embodiments, the surgical instruments and the tissue sensor described herein may comprise one or more processors (e.g., microprocessor, microcontroller, controller) coupled to various sensors. In addition, to the processor(s), a storage or non-transitory memory (having operating logic) and communication interface, are coupled to each other.

As described earlier, the sensors may be configured to detect and collect data associated with the surgical device. The processor processes the sensor data received from the sensor(s).

The processor may be configured to execute the operating logic. The processor may be any one of a number of single or multi-core processors known in the art. The storage may comprise volatile and non-volatile storage media configured to store persistent and temporal (working) copy of the operating logic.

In various embodiments, the operating logic may be configured to perform the initial processing and transmit the data to the computer hosting the application to determine and generate instructions. For these embodiments, the operating logic may be further configured to receive information from and provide feedback to a hosting computer. In alternate embodiments, the operating logic may be configured to assume a larger role in receiving information and determining the feedback. In either case, whether determined on its own or responsive to instructions from a hosting computer, the operating logic may be further configured to control and provide feedback to the user.

In various embodiments, the operating logic may be implemented in instructions supported by the instruction set architecture (ISA) of the processor, or in higher level languages and compiled into the supported ISA. The operating logic may comprise one or more logic units or modules. The operating logic may be implemented in an object oriented manner. The operating logic may be configured to be executed in a multi-tasking and/or multi-thread manner. In other embodiments, the operating logic may be implemented in hardware such as a gate array.

In various embodiments, the communication interface may be configured to facilitate communication between a peripheral device and the computing system. The communication may include transmission of the collected biometric data associated with position, posture, and/or movement data of the user's body part(s) to a hosting computer, and transmission of data associated with the tactile feedback from the host computer to the peripheral device. In various embodiments, the communication interface may be a wired or a wireless communication interface. An example of a wired communication interface may include, but is not limited to, a Universal Serial Bus (USB) interface. An example of a wireless communication interface may include, but is not limited to, a Bluetooth interface.

For various embodiments, the processor may be packaged together with the operating logic. In various embodiments, the processor may be packaged together with the operating logic to form a SiP. In various embodiments, the processor may be integrated on the same die with the operating logic. In various embodiments, the processor may be packaged together with the operating logic to form a System on Chip (SoC).

Various embodiments may be described herein in the general context of computer executable instructions, such as software, program modules, and/or engines being executed by a processor. Generally, software, program modules, and/or engines include any software element arranged to perform particular operations or implement particular abstract data types. Software, program modules, and/or engines can include routines, programs, objects, components, data structures and the like that when executed by the processor, cause the processor to perform particular tasks or implement particular abstract data types. An implementation of the software, program modules, and/or engines components and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, program modules, and/or engines may be located in both local and remote computer storage media including memory storage devices. A memory such as a random access memory (RAM) or other dynamic storage device may be employed for storing information and instructions to be executed by the processor. The memory also may be used for storing temporary variables or other intermediate information during execution of instructions to be executed by the processor.

Although some embodiments may be illustrated and described as comprising functional components, software, engines, and/or modules performing various operations, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other embodiments, the functional components such as software, engines, and/or modules may be implemented by hardware elements that may include processors, microprocessors, circuits, circuit elements (e.g., transistors, resistors, capacitors, inductors, and so forth), integrated circuits, ASICs, PLDs, DSPs, FPGAs, logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more of the modules described herein may comprise one or more embedded applications implemented as firmware, software, hardware, or any combination thereof. One or more of the modules described herein may comprise various executable modules such as software, programs, data, drivers, application APIs, and so forth. The firmware may be stored in a memory of the controller and/or the controller which may comprise a nonvolatile memory (NVM), such as in bit-masked ROM or flash memory. In various implementations, storing the firmware in ROM may preserve flash memory. The NVM may comprise other types of memory including, for example, programmable ROM (PROM), erasable programmable ROM (EPROM), EEPROM, or battery backed RAM such as dynamic RAM (DRAM), Double-Data-Rate DRAM (DDRAM), and/or synchronous DRAM (SDRAM).

In some cases, various embodiments may be implemented as an article of manufacture. The article of manufacture may include a computer readable storage medium arranged to store logic, instructions and/or data for performing various operations of one or more embodiments. In various embodiments, for example, the article of manufacture may comprise a magnetic disk, optical disk, flash memory or firmware containing computer program instructions suitable for execution by a general purpose processor or application specific processor. The embodiments, however, are not limited in this context.

The functions of the various functional elements, logical blocks, modules, and circuits elements described in connection with the embodiments disclosed herein may be implemented in the general context of computer executable instructions, such as software, control modules, logic, and/or logic modules executed by the processing unit. Generally, software, control modules, logic, and/or logic modules comprise any software element arranged to perform particular operations. Software, control modules, logic, and/or logic modules can comprise routines, programs, objects, components, data structures and the like that perform particular tasks or implement particular abstract data types. An implementation of the software, control modules, logic, and/or logic modules and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, control modules, logic, and/or logic modules may be located in both local and remote computer storage media including memory storage devices.

Additionally, it is to be appreciated that the embodiments described herein illustrate example implementations, and that the functional elements, logical blocks, modules, and circuits elements may be implemented in various other ways which are consistent with the described embodiments. Furthermore, the operations performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual embodiments described and illustrated herein has discrete components and features which may be readily separated from or combined with the features of any of the other several aspects without departing from the scope of the present disclosure. Any recited method can be carried out in the order of events recited or in any other order which is logically possible.

It is worthy to note that any reference to "one embodiment" or "an embodiment" means that a particular feature, structure, or characteristic described in connection with the embodiment is comprised in at least one embodiment. The appearances of the phrase "in one embodiment" or "in one aspect" in the specification are not necessarily all referring to the same embodiment.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

It is worthy to note that some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, API, exchanging messages, and so forth.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The disclosed embodiments have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and when necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely examples and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that when a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even when a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

VI. Examples of Combinations

The following examples/clauses relate to various non-exhaustive ways in which the teachings herein may be combined or applied. It should be understood that the following examples/clauses are not intended to restrict the coverage of any claims that may be presented at any time in this application or in subsequent filings of this application. No disclaimer is intended. The following examples/clauses are being provided for nothing more than merely illustrative purposes. It is contemplated that the various teachings herein may be arranged and applied in numerous other ways. It is also contemplated that some variations may omit certain features referred to in the below examples/clauses. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

1. A tissue sensor configured to be used with a surgical stapler and tissue of a body, the tissue sensor comprising:
   a flexible substrate configured to be disposed between the tissue and the surgical stapler, wherein the surgical stapler is configured to be actuated to clamp the tissue and the tissue sensor together;
   a sensor array comprising sensors disposed on the flexible substrate, wherein the sensor array is configured to sense a parameter and generate a signal indicative thereof in response to a clamping force that is applied by the surgical stapler to clamp the tissue and the tissue sensor together; and
   a controller disposed in or on the flexible substrate, the controller coupled with the sensor array and configured to:
      receive the signal from the sensor array;
      process the signal to determine a measurement of the parameter based on the processed signal; and provide an indication of the measurement of the parameter to a user of the surgical stapler.

2. The tissue sensor of claim 1, further comprising a transmitter coupled with the controller and disposed in or on the flexible substrate, wherein the transmitter is configured to transmit the processed signal to a processor of a computer coupled with the surgical stapler.

3. The tissue sensor of claim 2, wherein the processor is configured to cause the measurement of the parameter to be displayed on a display coupled with the computer.

4. The tissue sensor of claim 1, wherein the tissue sensor is configured to be disposed laying on a surface of the tissue such that the tissue sensor is between the tissue and the surgical stapler.

5. The tissue sensor of claim 1, wherein the parameter is indicative of characteristics of the tissue, a clamping condition, a location condition, or combinations thereof.

6. The tissue sensor of claim 5, wherein the clamping condition is indicative of an amount of pressure that is exerted by the surgical stapler on the clamped tissue and the tissue sensor.

7. The tissue sensor of claim 1, wherein the controller is configured to adjust the measurement of the parameter based on the processed signal as the tissue is being clamped over time, the adjusted measurement dynamically varying based on the clamping of the tissue, wherein a current value of the adjusted measurement is indicative of tissue characteristics, clamping positioning, or tissue characteristics and clamping positioning at a time of measurement.

8. The tissue sensor of claim 1, wherein an operation of the surgical stapler is adjusted by the user as a function of the measurement of the parameter.

9. The tissue sensor of claim 1, wherein the controller is configured to, based on the processed signal, determine a measurement of the clamping force applied by the surgical stapler to clamp the tissue and the tissue sensor together.

10. The tissue sensor of claim 1, wherein the controller is configured to, based on the processed signal, determine a location of the clamped tissue between proximal and distal ends of the surgical stapler.

11. The tissue sensor of claim 1, wherein the controller is configured to, based on the processed signal, determine various characteristics of the tissue.

12. The tissue sensor of claim 1,
wherein the tissue sensor further includes a transmitter,
wherein the surgical stapler further includes a shaft coupled with an end effector extending distally from the shaft,
wherein the transmitter transmits the processed signal to a signal relay disposed in the end effector, and
wherein the signal relay routes the processed signal to a router disposed in a proximal end of the shaft, the router being operable to transmit the processed signal to a processor of a computer.

13. The tissue sensor of claim 1, wherein the sensors comprise force sensors, location sensors, or combinations thereof.

14. A tissue sensor configured to be used with a surgical stapling instrument and tissue of a body, the tissue sensor comprising:
a flexible substrate configured to be disposed on opposite surfaces of the tissue, such that the flexible substrate is disposed between the tissue and jaws of the surgical stapling instrument, wherein the jaws of the surgical stapling instrument comprise a first jaw pivotably coupled at a proximal end thereof with a second jaw, and wherein the surgical stapling instrument is configured to be actuated to pivot one of the first or second jaw relative to the other of the first or second jaw to clamp the tissue and the flexible substrate together;
a sensor array comprising sensors disposed on the flexible substrate, wherein the sensor array is configured to sense a parameter and generate a signal indicative thereof in response to a clamping force that is applied by the surgical stapling instrument to clamp the tissue and the tissue sensor together; and
a controller disposed in or on the flexible substrate, the controller coupled with the sensor array and configured to:
receive the signal from the sensor array;
process the signal to determine a measurement of the parameter based on the processed signal; and
provide an indication of the measurement of the parameter to a user of the surgical stapling instrument.

15. The tissue sensor of claim 14, further comprising a transmitter coupled with the controller and disposed in or on the flexible substrate, wherein the transmitter is configured to transmit the signal to a processor of a computer.

16. The tissue sensor of claim 15, wherein the processor is configured to cause the measurement of the parameter to be displayed on a display coupled with the computer.

17. The tissue sensor of claim 14, wherein the parameter is indicative of a clamping condition, a distance condition of the first and second jaws, or a location condition of the first and second jaws, or combinations thereof.

18. The tissue sensor of claim 14, wherein the controller is configured to, based on the processed signal, determine a measurement of a distance between a distal end of the first jaw and a distal end of the second jaw when the tissue is clamped.

19. The tissue sensor of claim 18, wherein the controller is configured to, based on the measurement of the distance, determine a thickness or compressibility of the clamped tissue.

20. The tissue sensor of claim 14, wherein the sensors comprise proximity sensors including magnetic, optical, or Hall effect sensors, or combinations thereof.

21. The tissue sensor of claim 14, wherein the sensors comprise force sensors, proximity sensors, location sensors, or combinations thereof.

22. A method for determining characteristics of a tissue, the method comprising:
disposing a tissue sensor on the tissue;
clamping, by a surgical stapler, the tissue sensor and the tissue together;
sensing, by the tissue sensor disposed on the tissue, a force as input in response to the clamping of the tissue and the tissue sensor;
converting, by the tissue sensor, the force to an electrical output signal indicative of a thickness of the tissue;
transmitting, by the tissue sensor to a processor, the electrical output signal; and
controlling, by the processor, the surgical stapler based on the electrical output signal.

23. The method of claim 22, further comprising:

unclamping the surgical stapler from the tissue sensor and the tissue to allow the tissue sensor to be removed; and re-clamping, by the surgical stapler, the tissue for transection.

VII. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. Pat. App. No. 63/467,622, entitled "Surgical Stapler Cartridge Having Intermediate Raised Tissue Engagement Protrusions," filed on May 19, 2023; U.S. Pat. App. No. 63/467,623, entitled "Surgical Stapler Cartridge Having Tissue Engagement Protrusions with Enlarged Engagement Surface," filed on May 19, 2023; U.S. Pat. App. No. 63/467, 648, entitled "Surgical Stapler Cartridge Having Raised Surface to Promote Buttress Adhesion," filed on May 19, 2023; U.S. Pat. App. No. 63/467,469, entitled "Surgical Stapler Cartridge Having Cartridge Retention Features," filed on May 19, 2023; U.S. Pat. App. No. 63/459,739, entitled "Surgical Stapler Anvil Having Staple Forming Pockets with Laterally Varying Orientations," filed on May 19, 2023; U.S. Pat. App. No. 63/467,656, entitled "Surgical Stapler With Discretely Positionable Distal Tip," filed on May 19, 2023; and/or U.S. Pat. App. No. 63/467,615, entitled "Incompatible Staple Cartridge Use Prevention Features for Surgical Stapler," filed on May 19, 2023.

Additionally, any one or more of the teachings herein may be combined with any one or more of the teachings disclosed in U.S. Pat. App. No. 63/459,739, entitled "Surgical Stapler Anvil Having Staple Forming Pockets with Laterally Varying Orientations," filed on Apr. 17, 2023. The disclosure of each of these U.S. patent applications is incorporated by reference herein in its entirety.

Additionally, any one or more of the teachings herein may be combined with any one or more of the teachings disclosed in U.S. Pat. No. 11,304,697, entitled "Surgical Stapler with Deflectable Distal Tip," issued Apr. 19, 2022, the disclosure of which is incorporated by reference herein, in its entirety; U.S. Pat. No. 11,317,912, entitled "Surgical Stapler with Rotatable Distal Tip," issued May 3, 2022, the disclosure of which is incorporated by reference herein, in its entirety; and/or U.S. Pat. No. 11,439,391, entitled "Surgical Stapler with Toggling Distal Tip," issued Sep. 13, 2022, the disclosure of which is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A tissue sensor configured to be used with a surgical stapler and tissue of a body, the tissue sensor comprising:

a flexible substrate configured to be disposed between the tissue and the surgical stapler, wherein the surgical stapler is configured to be actuated to clamp the tissue and the tissue sensor together;

a sensor array comprising sensors disposed on the flexible substrate, wherein the sensor array is configured to sense a parameter and generate a signal indicative thereof in response to a clamping force that is applied by the surgical stapler to clamp the tissue and the tissue sensor together; and a controller disposed in or on the flexible substrate, the controller coupled with the sensor array and configured to:

receive the signal from the sensor array;

process the signal to determine a measurement of the parameter based on the processed signal; and provide an indication of the measurement of the parameter to a user of the surgical stapler.

2. The tissue sensor of claim 1, further comprising a transmitter coupled with the controller and disposed in or on the flexible substrate, wherein the transmitter is configured to transmit the processed signal to a processor of a computer coupled with the surgical stapler.

3. The tissue sensor of claim 2, wherein the processor is configured to cause the measurement of the parameter to be displayed on a display coupled with the computer.

4. The tissue sensor of claim 1, wherein the tissue sensor is configured to be disposed laying on a surface of the tissue such that the tissue sensor is between the tissue and the surgical stapler.

5. The tissue sensor of claim 1, wherein the parameter is indicative of characteristics of the tissue, a clamping condition, a location condition, or combinations thereof.

6. The tissue sensor of claim 5, wherein the clamping condition is indicative of an amount of pressure that is exerted by the surgical stapler on the clamped tissue and the tissue sensor.

7. The tissue sensor of claim 1, wherein the controller is configured to adjust the measurement of the parameter based on the processed signal as the tissue is being clamped over time, the adjusted measurement dynamically varying based on the clamping of the tissue, wherein a current value of the adjusted measurement is indicative of tissue characteristics, clamping positioning, or tissue characteristics and clamping positioning at a time of measurement.

8. The tissue sensor of claim 1, wherein an operation of the surgical stapler is adjusted by the user as a function of the measurement of the parameter.

9. The tissue sensor of claim 1, wherein the controller is configured to, based on the processed signal, determine a measurement of the clamping force applied by the surgical stapler to clamp the tissue and the tissue sensor together.

10. The tissue sensor of claim 1, wherein the controller is configured to, based on the processed signal, determine a location of the clamped tissue between proximal and distal ends of the surgical stapler.

11. The tissue sensor of claim 1, wherein the controller is configured to, based on the processed signal, determine various characteristics of the tissue.

12. The tissue sensor of claim 1, wherein the tissue sensor further includes a transmitter, wherein the surgical stapler further includes a shaft coupled with an end effector extending distally from the shaft, wherein the transmitter transmits the processed signal to a signal relay disposed in the end effector, and wherein the signal relay routes the processed signal to a router disposed in a proximal end of the shaft, the router being operable to transmit the processed signal to a processor of a computer.

13. The tissue sensor of claim 1, wherein the sensors comprise force sensors, location sensors, or combinations thereof.

14. A tissue sensor configured to be used with a surgical stapling instrument and tissue of a body, the tissue sensor comprising:

a flexible substrate configured to be disposed on opposite surfaces of the tissue, such that the flexible substrate is disposed between the tissue and jaws of the surgical stapling instrument, wherein the jaws of the surgical stapling instrument comprise a first jaw pivotably coupled at a proximal end thereof with a second jaw, and wherein the surgical stapling instrument is configured to be actuated to pivot one of the first or second jaw relative to the other of the first or second jaw to clamp the tissue and the flexible substrate together;

a sensor array comprising sensors disposed on the flexible substrate, wherein the sensor array is configured to sense a parameter and generate a signal indicative thereof in response to a clamping force that is applied by the surgical stapling instrument to clamp the tissue and the tissue sensor together; and a controller disposed in or on the flexible substrate, the controller coupled with the sensor array and configured to:

receive the signal from the sensor array;

process the signal to determine a measurement of the parameter based on the processed signal; and provide an indication of the measurement of the parameter to a user of the surgical stapling instrument.

15. The tissue sensor of claim 14, further comprising a transmitter coupled with the controller and disposed in or on the flexible substrate, wherein the transmitter is configured to transmit the signal to a processor of a computer.

16. The tissue sensor of claim 15, wherein the processor is configured to cause the measurement of the parameter to be displayed on a display coupled with the computer.

17. The tissue sensor of claim 14, wherein the parameter is indicative of a clamping condition, a distance condition of the first and second jaws, or a location condition of the first and second jaws, or combinations thereof.

18. The tissue sensor of claim 14, wherein the controller is configured to, based on the processed signal, determine a measurement of a distance between a distal end of the first jaw and a distal end of the second jaw when the tissue is clamped.

19. The tissue sensor of claim 18, wherein the controller is configured to, based on the measurement of the distance, determine a thickness or compressibility of the clamped tissue.

20. The tissue sensor of claim 14, wherein the sensors comprise proximity sensors including magnetic, optical, or Hall effect sensors, or combinations thereof.

21. The tissue sensor of claim 14, wherein the sensors comprise force sensors, proximity sensors, location sensors, or combinations thereof.

22. A method for determining characteristics of a tissue, the method comprising:

disposing a flexible substrate on the tissue, wherein a controller, a sensor array, and a transmitter are disposed in or on the flexible substrate;

clamping, by a surgical stapler, the flexible substrate and the tissue together;

sensing, by the sensor array, a force as input in response to the clamping of the tissue and the flexible substrate;

converting, by the controller, the force to an electrical output signal indicative of a thickness of the tissue;

transmitting, by the transmitter to a processor, the electrical output signal; and controlling, by the processor, the surgical stapler based on the electrical output signal.

23. The method of claim 22, further comprising:

unclamping the surgical stapler from the flexible substrate and the tissue to allow the flexible substrate to be removed; and re-clamping, by the surgical stapler, the tissue for transection.

\* \* \* \* \*